United States Patent
Gavish et al.

(10) Patent No.: US 11,861,885 B2
(45) Date of Patent: Jan. 2, 2024

(54) SYSTEM AND METHOD FOR CHARACTERIZATION OF CANNABACEAE PLANTS

(71) Applicants: Assaf Gavish, Rehovot (IL); Asaf Levy, Kidmat Tzvi (IL); Yoav Gavish, Rehovot (IL)

(72) Inventors: Assaf Gavish, Rehovot (IL); Asaf Levy, Kidmat Tzvi (IL); Yoav Gavish, Rehovot (IL)

(73) Assignee: MYCROPS TECHNOLOGIES LTD., Nes-Ziona (IL)

( * ) Notice: Subject to any disclaimer, the term of this patent is extended or adjusted under 35 U.S.C. 154(b) by 0 days.

(21) Appl. No.: 16/324,915

(22) PCT Filed: Sep. 4, 2017

(86) PCT No.: PCT/IL2017/050988
§ 371 (c)(1),
(2) Date: Feb. 12, 2019

(87) PCT Pub. No.: WO2018/042445
PCT Pub. Date: Mar. 8, 2018

(65) Prior Publication Data
US 2020/0327326 A1  Oct. 15, 2020

Related U.S. Application Data

(60) Provisional application No. 62/383,503, filed on Sep. 5, 2016.

(51) Int. Cl.
*G06V 10/82* (2022.01)
*A01H 6/28* (2018.01)
(Continued)

(52) U.S. Cl.
CPC ............ *G06V 10/82* (2022.01); *A01B 79/005* (2013.01); *A01H 6/28* (2018.05);
(Continued)

(58) Field of Classification Search
CPC .................................................. G06K 9/00657
See application file for complete search history.

(56) References Cited

U.S. PATENT DOCUMENTS 11,120,552 B2 * 9/2021 Weldemariam ........ G06N 5/022
2008/0037904 A1 * 2/2008 Hiramoto ............. G06K 9/2063
382/306

(Continued)

FOREIGN PATENT DOCUMENTS

EP    3529708    4/2018

OTHER PUBLICATIONS

Richard Augimen: "Question on ResearchGate.net forum: How does one calculate trichome density on plant material?", Apr. 4, 2016 (Apr. 4, 2016), XP055677679, Retrieved from the Internet: URL:https:// www.researchgate.net/post/ How_does_one_calculate_trichome_density_on_plant_material [retrieved on Mar. 18, 2020]; & Yan Cheng et al: "Analyses of Plant Leaf Cell Size, Density and Number, as Well as Trichome Number Using Cell Counter Plugin", Bio-Protocol, vol. 4, No. 13, Jul. 5, 2014 (Jul. 15, 2014), XP055677680, Sunnyvale, CA, USA.

(Continued)

*Primary Examiner* — Gandhi Thirugnanam
(74) *Attorney, Agent, or Firm* — Naomi S. Rosenman-Helfand

(57) ABSTRACT

A method and system for characterization of Cannabaceae plants using macro photography images is disclosed. The method comprises the steps of receiving one or more macro photography images of a Cannabaceae plant; performing feature extraction analysis of trichomes using image pro- (Continued)

cessing, and performing plant characterization analysis using a neural network which analyzes the macro photography images. The training phase of the neural network comprises using results of chemical composition laboratory tests performed on the plants for which the macro photography images have been used in the training phase. The invention calculates and reports an assessment of maturity of the plant for harvesting, diagnosis of the existence of diseases, insects, or pests, assessment of the presence and concentrations of central ingredients, recommendations for treatment during plants drying, curing or storage production processes, and assessment of the quality and pricing of Cannabaceae plants products.

21 Claims, 8 Drawing Sheets

(51) Int. Cl.
 *A01B 79/00* (2006.01)
 *G06V 20/10* (2022.01)
 *G06F 18/2413* (2023.01)
 *G06V 10/764* (2022.01)
 *G06V 20/60* (2022.01)

(52) U.S. Cl.
 CPC ...... *G06F 18/24143* (2023.01); *G06V 10/764* (2022.01); *G06V 20/188* (2022.01); *G06V 20/60* (2022.01)

(56) References Cited

U.S. PATENT DOCUMENTS

| | | | |
|---|---|---|---|
| 2008/0239293 A1* | 10/2008 | Fuchigami | G01N 21/3151 356/73 |
| 2009/0048107 A1* | 2/2009 | Johnson | A61K 36/87 504/117 |
| 2011/0174873 A1* | 7/2011 | Mori | A01G 9/088 235/375 |
| 2012/0109614 A1* | 5/2012 | Lindores | G06K 9/00657 703/11 |
| 2014/0259920 A1* | 9/2014 | Wilson | A01G 22/00 47/62 R |
| 2014/0287068 A1* | 9/2014 | Lewis | A01H 5/12 424/725 |
| 2014/0298511 A1* | 10/2014 | Lewis | A01H 5/10 800/260 |
| 2015/0366154 A1* | 12/2015 | Lewis | A01H 5/02 800/298 |
| 2016/0073955 A1 | 3/2016 | Salem | |
| 2018/0220589 A1* | 8/2018 | Burden | A01G 3/08 |
| 2019/0167177 A1* | 6/2019 | Evins | A61B 5/18 |
| 2019/0380278 A1* | 12/2019 | Burden | B25J 9/1005 |
| 2020/0117897 A1* | 4/2020 | Froloff | G06K 9/00657 |
| 2020/0253127 A1* | 8/2020 | McCall | G06K 9/6274 |
| 2020/0327326 A1* | 10/2020 | Gavish | G06K 9/6274 |
| 2021/0381961 A1* | 12/2021 | Smith | G01N 33/0098 |
| 2022/0051154 A1* | 2/2022 | Mueller-Sim | G06N 3/084 |

OTHER PUBLICATIONS

Anonymous: "When to harvest marijuana plants according to trichome ripeness—Alchimia blog", Apr. 11, 2016 (Apr. 11, 2016), XP055677531, Retrieved from the Internet: URL:http://web.archive.org/web/2016041111161 O/https://www.alchimiaweb.com/blogen/harvest-marijuana-plants-trichome-ripeness/ [retrieved on Mar. 18, 2020].

Bensch R et al: "Image analysis of *Arabidopsis trichome* patterning in 4D confocal datasets", Biomedical Imaging: From Nano to Macro, 2009. ISBI '09. IEEE International Symposium on, IEEE, Piscataway, NJ, USA, Jun. 28, 2009 (Jun. 28, 2009), pp. 742-745, XP031502146, ISBN: 978-1-4244-3931-7.

Srdjan Sladojevic et al: "Deep Neural Networks Based Recognition of Plant Diseases by Leaf Image Classification", Computational Intelligence and Neuroscience, May 29, 2016 (May 29, 2016), pp. 1-11, XP055385550, DOI: 10.1155/2016/3289801 Retrieved from the Internet: URL:http://downloads.hindawi.com/journals/cin/2016/3289801.pdf [retrieved on Jun. 27, 2017].

* cited by examiner

SYSTEM AND METHOD FOR CHARACTERIZATION OF CANNABACEAE PLANTS

FIELD OF THE INVENTION

The present invention, relates to a system and method for characterization of plants and, more particularly, to a system and method for characterization of plants that are members of the Cannabaceae family. More specifically, to characterization of plants from the genus of *Cannabis* and the species of *Cannabis sativa*.

BACKGROUND

Ingredients from plants that are members of the Cannabaceae family are used in many products such as beer, soap, flavors and ornamental materials, fibers that are used for ropes, clothes, food, paper, textiles and plastics, medications and recreational drugs (e.g., marijuana or hashish). Reliable characterization, diagnosis or assessment of the plant status is important to producers/cultivators as well as to traders such as wholesalers, retailers and end consumers. A reliable, unbiased, automatic (i.e., non-manual) assessment of the plant's maturity, the optimal harvesting time, the chemical composition, the estimated market value and the like, are highly desired.

It is time consuming and challenging to detect the maturity level, as even on a single plant, some flowers may be mature, while others need to be left on the plant to ripen for another week. Therefore, a grower cannot simply evaluate a single plant to detect the maturity level for an entire field.

Conventional manual methods for determining the plant's status (e.g., maturity, potency) utilize a magnifying tool (e.g., magnifying glass, jeweler's loupe, microscope) to visualize the status and color of the organelles termed "trichomes" on the Cannabaceae plant matter (leaf, flower etc.).

Many plants have trichomes covering different parts of the plant, in which secondary metabolites (chemicals) are produced, with known roles spanning from deterrence of herbivores, attraction of pollinators and protecting insects, UV filtration, physical (sticky) barriers to pests, among others. Trichomes are classified according to morphological traits into several groups.

In *Cannabis*, trichomes can be divided into these groups: simple unicellular, cystolythic, capitate sessile, antherial sessile, capitate stalked, and bulbous. Capitate stalked trichomes, also known as glandular stalked trichomes, are considered the major producers of the Active Pharmacological Ingredients (referred hereinafter as APIs), including THC, CBD, CBN and the other Cannabinoids, terpenes and flavonoids.

Generally, they consist of a multicellular stalk-like structure, on top of which a spherical gland is positions, the stalk is typically 100-500 um in length, while the gland (also called resin head) is typically 25-100 um in diameter.

Most *Cannabis* strains have massive amounts of trichomes on all above-ground parts of the plant, mostly concentrated on the flowering part of the female plant. These flowers are harvested as either a final product, or undergo post-harvest processing, such as production of concentrates.

Unlike most plants, in *Cannabis* the APIs are concentrated at close to pure state in definite loci, inside the trichome heads. Moreover, the resin heads in which the APIs are produced and accumulated are see-through. Some of the APIs have color/affect coloration of the resin head as they change in concentration. This unique feature allows a direct visualization of some APIs in the resin head, to the extent that in some cases an optical magnification in visual light is enough for a direct observation of a change in the concentration of the APIs.

Trichomes exist in many shapes and sizes, but there are three that appear most often on *Cannabis* plants:
(1) Bulbous trichomes are the smallest of the bunch, and they appear on the surface of the entire plant. Bulbous trichomes are as small as 10-15 micrometers, which is tiny enough to only be comprised of a handful of cells;
(2) Capitate sessile trichomes are slightly larger and contain larger glandular head of 25-100 micrometers in diameter;
(3) Capitate-stalked trichomes, which have a glandular head with 25-100 micrometers in diameter, also have a stalk-like multicellular structure, and range from anywhere between 100-500 um in length, meaning they're much larger and can actually be seen by the naked eye. Their gland heads contains the major THC and CBD composition.

Cannabinoid synthesis within the trichome begins as *Cannabis* plants move into their bloom phase. As they begin to produce flowers, trichomes form along the outer surface of the above-ground plant vegetation and begin to transport vacuoles and plastids from their stalk and secretory 'disc cells' within the glandular head, into the expanding gland head cavity. At this point, cells within the gland head will begin to metabolize and form precursors for what will eventually become Cannabinoids, and export them in vacuoles and plastids into the gland-head cavity, where different precursors interact to form Cannabinoids.

While the chemical precursors for the creation of the APIs are absorbed through the roots from the soil and are found throughout the plant, Cannabinoids and terpenes are manufactured within the trichomes by a rosette of cells at the base of each trichome head, called disk cells. The capitate-stalked trichomes are characterized by a secretory disc of one to 13 cells supported by a layer of stipe cells above a layer of base cells embedded in the epidermis. The secretory cells of mature glandular trichomes produce a resinous fluid which accumulates beneath a membranous sheath. Trichomes occur at various sizes, concentrations and stages of maturity, in greater amounts nearer the top of the plant on the flowering buds, and as the plants mature.

The rate and concentration at which a *Cannabis* plant produces trichomes will be contingent on both genetics well as some environmental factors. Though plants containing higher concentrations of trichomes don't always produce the highest concentration of Cannabinoids and/or terpenes, variables such as UV light greatly affect Cannabinoid and terpene synthesis within the trichome head. Typically, plants that receive a broader spectrum of light will produce higher concentrations of Cannabinoids, though in many cases these reactions will be strain-specific.

A trichome's lifecycle largely parallels that of the *Cannabis* plant on which it resides, making it incredibly valuable for farmers to monitor. The life of a trichome can be analogous to a parabola, where the apex represents the point at which maturation exceeds and degradation begins. For the most part, trichomes will display maturation on this parabola by changing opacity from a clear translucent state to a cloudy white and, later on, amber hue.

This transition of color within a trichome head represents its peak ripeness and farmers typically use this as a sign to harvest, as it's the point when the trichome has reached full maturation and will begin to degrade from this point forward. It is important to understand that not all strains of *Cannabis* are the same and some trichomes will display maturation differently.

Whether alive on a stalk or harvested, trichomes are incredibly volatile and risk destruction and/or degradation at the hands of many catalysts, including but not limited to: Physical contact or agitation, Heat, Light, Oxygen and Time. Not only do the trichomes themselves risk damage when exposed to these elements, but the essential oils within them risk degradation.

It is good practice for quality assessment, to inspect the trichomes on the flowers in order to assess the plant's maturity/potency potential, and to determine the plant maturity using, for instance, the density, size, shape and color of these trichomes.

Manual analysis or assessment is inherently limited since it necessitates an expert to manually observe the plant's trichomes (either directly through the optical apparatus or by inspecting trichome micrographs). Consequently: (1) Trichome diagnostics is slow and costly and serves as a bottle neck in the industrial agriculture process and trade scenarios, resulting in low sample checking (as opposed to checking each plant or even each flower), (2) Novice or home growers lack the required expertise and refer to unaccountable sources.

The consequence of these two problems may cause wrong harvest timing which yields inferior end products.

Moreover, in a commerce scenario the product evaluation process is lacking due to the existing batch testing system, misleading both for the seller and buyer. Price is determined after a subjective assessment of quality, since the appropriate supply and demand category for that product is wrongfully appreciated.

It is an object of the invention to provide a reliable, unbiased, automatic assessment of plants that are members of the Cannabaceae family.

SUMMARY OF THE INVENTION

The invention provides a reliable, unbiased, automatic assessment of plants that are members of the Cannabaceae family.

According to some embodiments of the invention, there is provided a system configured to diagnose *Cannabis sativa* spp. plant status automatically by the analysis of plant images, while accumulating the analysis' results in databases. This is advantageous for plant e.g. *Cannabis* evaluation for cultivation and chemical composition of the finished product. For cultivators such a decision support system may consist of at least one of: (a) determining the plant's maturity, (b) determining harvesting time, (c) determining drying and curing processes progression (by means of trichomes inspection).

According to some embodiments of the invention, there is provided a system and method to assess the finished product for chemical composition aspect affects (i.e., potency) for *Cannabis* producers/cultivators and traders (wholesalers, retailers and end consumers) by evaluation of the plant's worth/value and/or the mode/dosage of consumption.

According to some embodiments of the invention, there is provided a service which can be accessed by end users using any suitable technology, for example using mobile phones and a downloaded smartphone app and/or via a website, thereby allowing *Cannabis* plant farmers/growers to upload acquired images of the *Cannabis* plant, and generating an estimate of plant maturity to return to the growers, helping them to optimize harvesting time. According to an aspect of some embodiments plant maturity estimates may be derived from image/s, either locally or on a cloud.

According to an aspect of some embodiments the system provides automated plant diagnosis.

According to an aspect of some embodiments the system provides an enhanced level of plant checking, eliminating the need for doing only batch-testing.

According to an aspect of some embodiments the system provides a decision support system aiding non-experts with agricultural decisions.

According to an aspect of some embodiments the system provides access between growers and potential products suitable for them.

According to an aspect of some embodiments the system provides a better diagnostics tool to serve plant cultivators, and/or scientists in the field of plant sciences, and/or merchants and consumers seeking to test the plant (e.g., *Cannabis*) product in order to evaluate its market price for sell or buy transactions.

According to an aspect of some embodiments of the present invention there is provided a system comprising machine vision (i.e., image analysis) on plant micrographs showing trichomes—to automatically detect the density, size, shape, and color of these trichomes. The results from this automated analysis could be either translated into a diagnosis regarding the plant status (relying on researched metrics of relations between trichome and plant states or lab tests of the photographed plants) or used in a predefined rule-set that was created by the user. Each plant's results over time is combined to create an ongoing plant status dynamics, which can be used while the plant is being grown to detect problems in maturation (and others) and most importantly help determine the harvest timing to yield the wanted trichome state at time of harvest.

Additionally, trichome detection can aid post-harvest processing stages that are critical to the quality of the end product, like drying, curing, and storage. An automated tracking of the change in these parameters (such as the one suggested in this application) in post-harvest stages could help to fine-tune and automate these stages. In a trading scenario, the suggested machine vision system allows a fast, low-cost, and non-destructive potency testing solution. In the US *Cannabis* market, as well as in other countries, price is affected by potency. The suggested system allows the buyer and seller to detect potency on the spot prior to/after the sale has been made, thus enabling an objective assessment of potency and appropriate price group (after factoring in the supply and demand metrics for that potency group). According to an aspect of some embodiments the system developed as part of the trichome identification process may serve as a holistic solution to all agricultural and trade-related diagnoses that demand micro-scale observations, such as mold and other diseases and pests identification.

According to an aspect of some embodiments of the present invention there is provided a method for characterization of Cannabaceae plants using macro photography images, the method comprises the steps of: (a) receiving one or more macro photography images of Cannabaceae plant; (b) performing at least one of or the combination of: (1) feature extraction analysis of trichomes in said macro photography images using image processing; and (2) plants characterization analysis using neural network that is provided with input vector comprising the macro photography images, wherein the training phase of said neural network comprises using results of chemical composition lab tests performed on the plants for which the macro photography images has been used in the training phase; (c) conditioned upon the products of step (b), calculating and reporting an assessment for at least one of or any combination of: maturity of the plant for harvesting; diagnosis of the existence of diseases, insects, or pests; assessment of at least one of or any combination of Cannabaceae plants Cannabinoid, terpene or flavonoid ingredients concentrations; recommendations for treatments during plants drying, curing or storage production processes; and assessment of Cannabaceae plants products quality and price.

According to some embodiments of the invention, the feature extraction analysis of trichomes includes analysis of at least one of: number, size, shape and color of trichomes.

According to some embodiments of the invention, the analysis further comprising: detecting leaf colors.

According to some embodiments of the invention, the analysis further comprises detecting the growth rate by at least one of: plant shape and movement over time.

According to some embodiments of the invention, calculating and reporting an assessment further comprises at least one of or any combination of: detection of mold; recommendations for irrigation and plant treatments; detection of nutrient deficiencies; detection of nutrient excesses; assessment of turgor (water pressure); assessment of plant gender/sex organs.

According to some embodiments of the invention, the method further comprises functionality for phenotyping support for breeders.

According to some embodiments of the invention, the assessment further comprises facilitation of flower drying, curing, and storing or any combination thereof.

According to some embodiments of the invention, macro photography images captured using spectrum band that are not in the visual spectrum or wider than the visual spectrum.

According to some embodiments of the invention, the analysis using neural network is performed by a plurality of neural networks connected in serial or calculates final products using post processing stage after running in parallel.

According to some embodiments of the invention, the method further comprises receiving non-macro photography images and auxiliary data of the plant and the image taking environment.

According to some embodiments of the invention, the method further comprises receiving a video capture or a 3D image capture of the plant.

According to some embodiments of the invention, the analysis step further comprises at least one of or a combination of (1) 3D image analysis, and (2) 3D modeling.

According to some embodiments of the invention, the method is further comprises receiving at least one of or a combination of (1) the name, ID and type of the user uploading the data; (2) the name, ID and type of the identity of the previous link in the distribution chain; and (3) the commercial name of the product.

According to an aspect of some embodiments of the present invention there is provided a system for characterization of Cannabaceae plants comprising: one or more macro photographic imager; one or more user terminals receiving images data from said one or more macro photographic imager; and a computing subsystem comprising one or more processors and communication links connecting said one or more user terminals to said one or more processors, wherein the one or more processors are configured to perform the following steps: receiving from the user terminals one or more macro photography images of Cannabaceae plant; performing at least one of or the combination of: feature extraction analysis of trichomes in said macro photography images using image processing; and plants characterization analysis using neural network that is provided with input vector comprising the macro photography images, wherein the training phase of said neural network comprises using results of chemical composition lab tests performed on the plants for which the macro photography images has been used in the training phase; conditioned upon the products of the analysis, calculating and reporting to the user terminals an assessment for at least one of or any combination of: maturity of the plant for harvesting; diagnosis of the existence of diseases, insects, or pests; assessment of at least one of or any combination of Cannabaceae plants Cannabinoid, terpene or flavonoid ingredients concentrations; recommendations for treatments during plants drying, curing or storage production processes; and assessment of Cannabaceae plants products quality and price.

According to some embodiments of the invention, the user terminal is a mobile phone, a smartphone or a tablet.

According to some embodiments of the invention, the communication links comprises at least one of or a combination of personal area network, local area network, wide area network and the Internet.

According to some embodiments of the invention, the processing subsystem is located inside or adjacent to the user terminal.

According to some embodiments of the invention, the processing subsystem is located in a remote server farm or in the cloud.

According to some embodiments of the invention, the system includes functionality for automated pre-purchase testing.

According to some embodiments of the invention, the macro photographic imager comprises of a camera subsystem of a smartphone and an optical magnification device that is adapted to be clipped-on to the said smartphone, and wherein the user terminal is implemented by the said smartphone.

According to some embodiments of the invention, images data is transferred from the macro photographic imager to the user terminal by WiFi, Bluetooth, or any other wireless communication link or USB, Ethernet or any other wire communication link.

According to an aspect of some embodiments of the present invention there is provided a non-transitory computer readable medium storing a program causing a computer to execute the method of characterization of Cannabaceae plants of claim 1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to a system and method for characterization of plants and, more particularly, but not exclusively, to a system and method for characterization plants that are members of the Cannabaceae family, and more specifically the genus of *Cannabis* and the species of *Cannabis sativa*.

The invention provides a reliable, unbiased, automatic assessment of the status of plants that are members of the Cannabaceae family.

Some embodiments of the invention provide a system configured to diagnose *Cannabis sativa* plant status, automatically, by analysis of plant images, while accumulating the analysis' results in databases.

This is advantageous for evaluation of the plant, e.g. *Cannabis*, for cultivation purposes, and to detect the chemical composition of the finished product. For cultivators such a decision support system may consist of at least one of: (a) determining the plant's maturity, (b) determining harvesting time, (c) determining progression of the drying and curing processes (by means of trichomes inspection).

Some embodiments of the invention, allow one to assess the chemical composition of the finished product (i.e., for potency) to determine the plant's worth/value and/or the mode/dosage of consumption.

Figure 1:
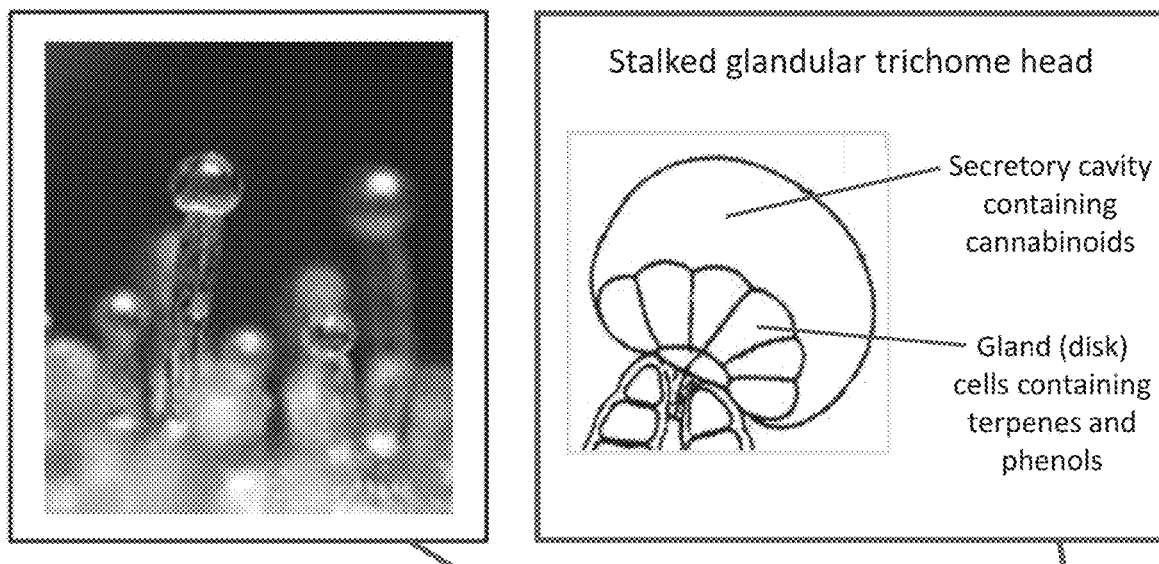
FIG. 1 shows the structure of a *Cannabis* plant.
Figure 1:
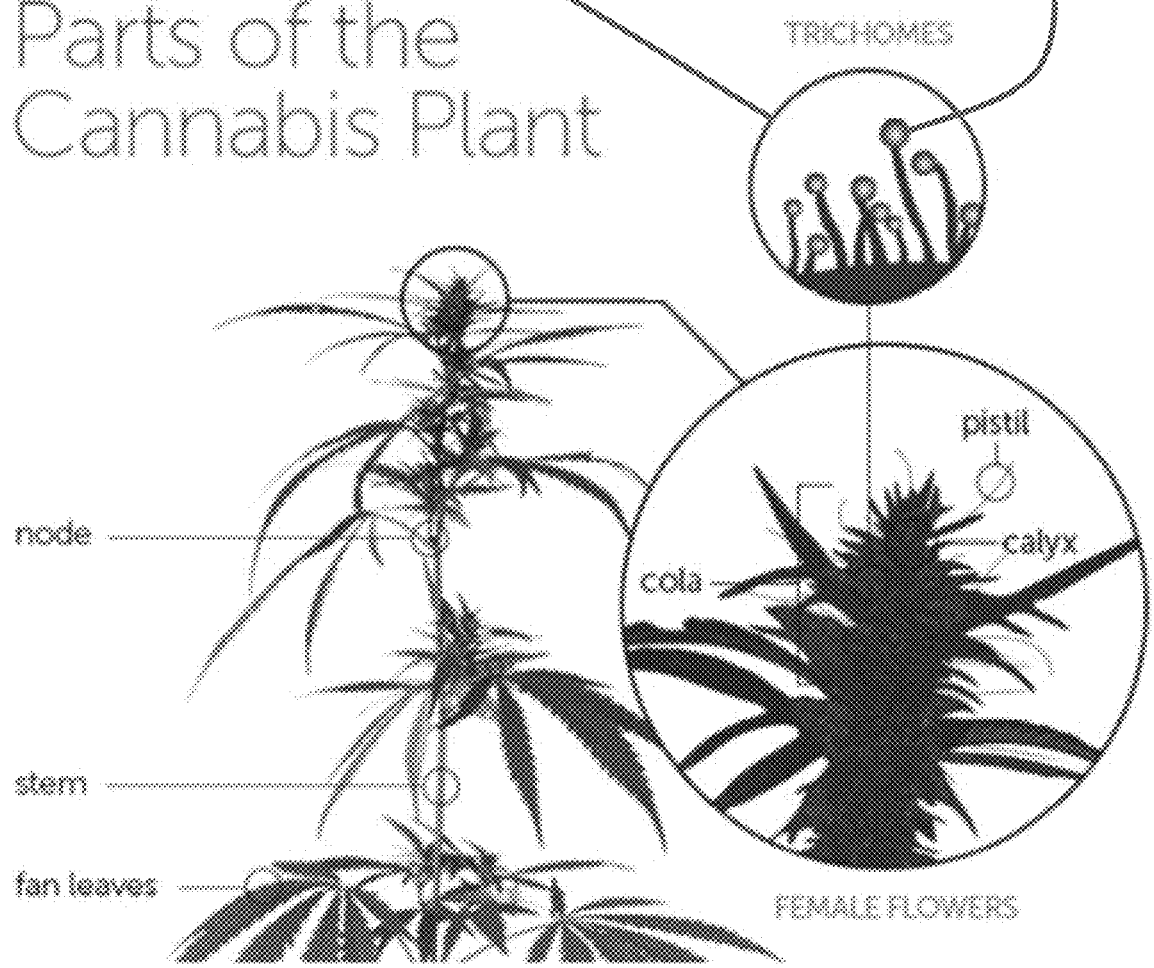

Referring to FIG. 1 of the drawings, reference is first made to the structure of *Cannabis* plant as illustrated in FIG. 1.

As illustrated, the *Cannabis* plant has leaves, stem, nodes and flowers. The female flowers (enlarged in the bottom right circle) are the parts that contain the majority of the Active Pharmacological Ingredients (APIs), e.g., psychoactive compounds. In the top left square, an actual image of a portion of the flower is provided. Further zooming in, the flowers and the leaves contain a forest-like resin glands known as trichomes. The trichomes (enlarged in the middle right circle) contain the active chemical compounds. In the top right square, an actual magnified image of few trichomes is provided.

The main psychoactive constituent of trichomes is tetrahydroCannabinol (THC). The *Cannabis* plant contains more than 500 compounds, among them at least 113 Cannabinoids. Besides THC, and Cannabidiol (CBD), most of the Cannabinoids are only produced in trace amounts. CBD is not psychoactive but has been shown to have medicinal positive effects and to modify the effect of THC in the nervous system. Differences in the chemical composition of *Cannabis* varieties, may produce different effects in humans.

As used herein, the term "Trichomes" means fine outgrowths or appendages found on plants of the Cannabaceae family, e.g., *Cannabis* plants.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2:
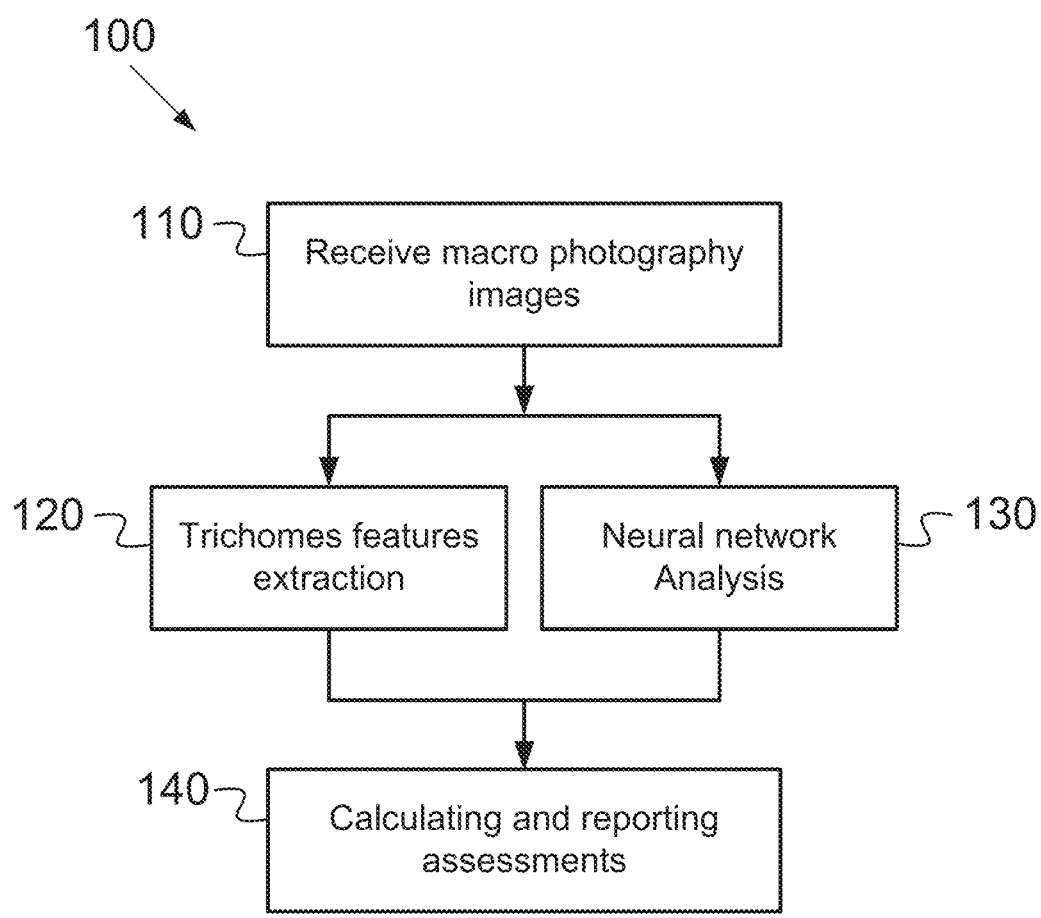
FIG. 2 is a simplified flow chart of a method for characterization of Cannabaceae plants using macro photography images.

Referring is now made to FIG. 2. FIG. 2 illustrates a simplified flow chart of a method for characterization of Cannabaceae plants using macro photography images. The method 100 comprises three steps: (a) receiving one or more macro photography images of Cannabaceae plant 110; (b) performing analysis based on the images (120 and 130); and (c) conditioned upon the products of step (b), calculating and reporting an assessment for the plant under characterization 140.

The input images in step 110 are macro photography images.

As used herein, the term "macro photography images" means an image with pixel size of less than 100 um×100 um and field of view of more than 1 mm×1 mm, i.e., image size (or image resolution) of at least 10×10 pixels.

Typically, macro photography images will have a pixel size of 10 um×10 um or less, and an image resolution of 1000×1000 pixels or more. An image resolution of 1000×1000 with 10 um×10 um pixel size provides a field of view of 10 mm×10 mm.

In an exemplary embodiment of the invention, Step 110 is receipt of a plurality of macro photography images. In this case, each image is analyzed separately and the assessment is done based on the plurality of analyzed products. Alternatively, the plurality of images is combined, e.g., generating a montage, and the analysis is performed over the combined image. The logic behind using the macro photography images is to be able to detect plant organelles, such as trichomes, which are typically 100-400 um long, and 100 um wide.

In an exemplary embodiment of the invention, the images contain a spectral band that is not in the visible spectrum such as IR band or UV band and the like. Alternatively, the spectrum band is wider than the visible spectrum. In an exemplary embodiment of the invention, a non-visible spectrum light sensor (spectrometer) may be used to detect additional information on the formation of the sampled material (e.g., UV, NIR).

The analysis step may be performed using several images and digital processing techniques. In step 120, feature extraction analysis of the trichomes, as viewed in the macro photography images, is performed using image processing.

An image processing algorithm identifies the trichomes and measures the trichomes density, shape, size, color, and the like. These values (both the average and the statistics) are transferred to step 140 for the final assessment. In step 130, analysis is performed, using a neural network (e.g., deep learning). The input may comprise of raw image or images that are converted to an input vector for the neural network. Additionally, the input may be the output of step 120.

The neural network weights (or coefficients) setting is based on a preliminary training phase of the neural network. The training phase comprises using results of lab tests performed on the plants in which the chemical composition and concentrations of central ingredients was analyzed, for plants used to obtain the macro photography images used in the training phase.

The outputs of the neural network can be any characteristic of the plant under analysis. For example, the output may be an estimation of a THC concentration. Alternatively, it can be an estimation of the probability the plant has a THC concentration in the range between 10%-20%.

In another option, the neural network output can be a quality ranking of between 0-100.

The neural network of step 130 may be comprised of several neural networks each performing part of the full analysis. These networks may be connected in serial or may be used to calculate the final products using post processing stage after running the networks in parallel.

In an exemplary embodiment of the invention, the analysis stage is based only on step 120. Alternatively, the analysis stage is based only on step 130.

In an exemplary embodiment of the invention, analysis is based on both step 120 and step 130. Additionally, analysis may be based on other auxiliary analysis techniques as disclosed later on. Additionally, the products of step 120 can be used as input for step 130.

Step 140, receives the analysis products of steps 120 and 130. Step 140 calculates and reports an assessment for at least one of or any combination of:

Maturity of the plant for harvesting.
Diagnosis of the existence of diseases, insects, or pests.
Recommendations for irrigation and plant treatments.
Recommendations for treatments during plant drying, curing, storage or production processes.
Assessment of post-production Cannabaceae plant product quality and price.
Assessment of at least one of or any combination of Cannabaceae plants Cannabinoid, terpene or flavonoid ingredient concentrations.

The calculation is performed based on the raw data coming from analysis steps 120 and 130. For example, the maturity for harvesting may be determined by the density, average size and average color of the trichomes appearing in the analyzed images and provided by step 120.

A multi-dimensional threshold may be set and then checked during step 140. For example, if the threshold is passed an instruction to harvesting the plant is provided by step 140 of method 100.

In another example, step 130 provides the probabilities of THC concentration in the plant. The probabilities are classified into ranges between 0-10%, 10%-20%, 20%-30%, and over 30%.

Step 140 calculates an assessment of the market price for this plant based on a linear or non-linear regression formula of the product of step 130.

Yet in another example, step 130 provides an estimation of the THC concentration in the trichomes, and step 140 rates the quality of the plant by adjusting this THC concentration with the average density of trichomes in the plant under analysis provided by step 120.

Further discussion on the specific types of assessments as well as other optional assessment will be disclosed hereinafter.

Figure 3:
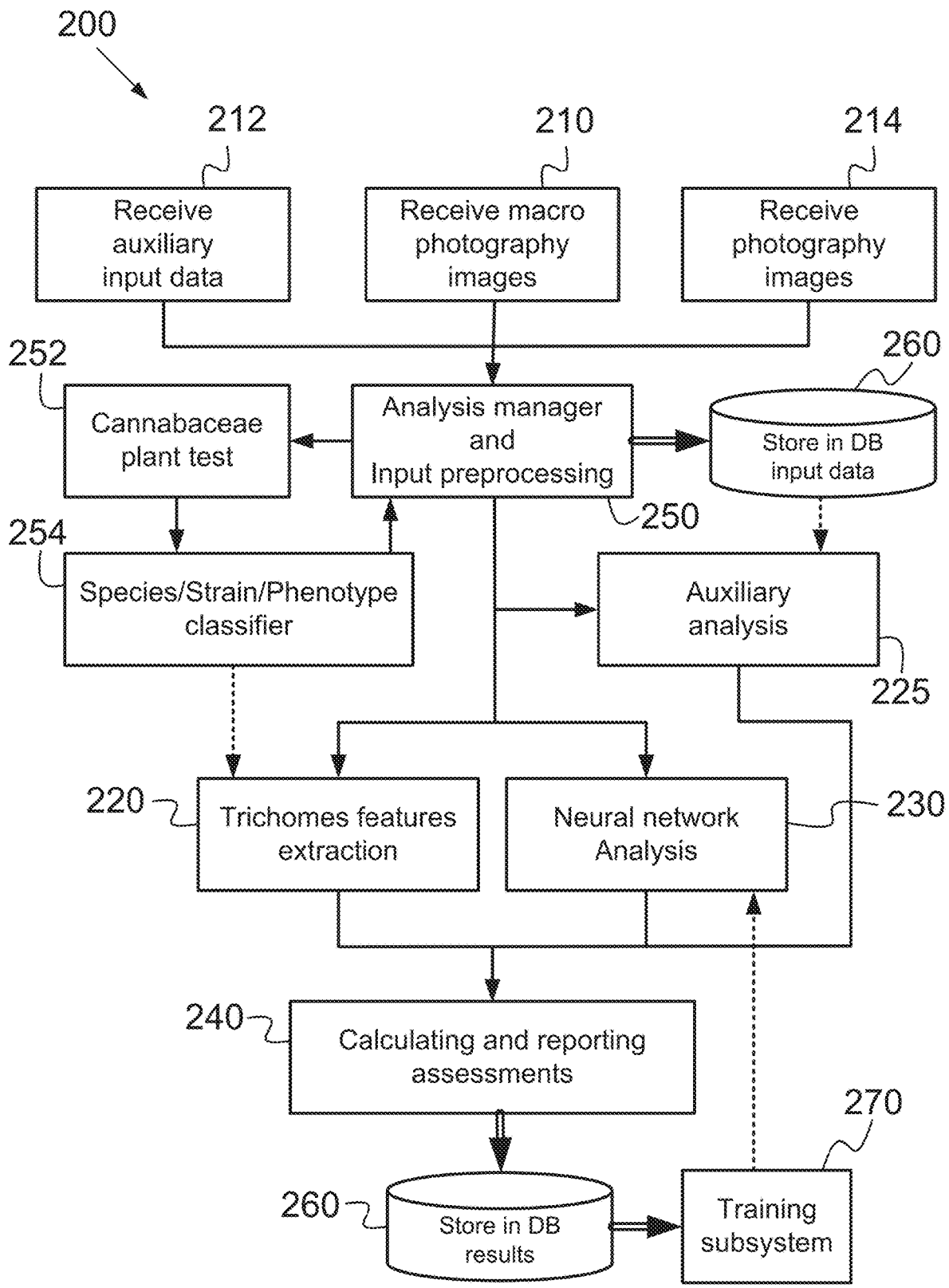
FIG. 3 is a more complete flow chart of a method for characterization of Cannabaceae plants using macro photography images.

Referring is now made to FIG. 3. FIG. 3 illustrates a more complete flow chart of a method for characterization of Cannabaceae plants using macro photography images.

The method, 200, comprises steps 210, 220, 230, 240 that are similar to steps 110, 120, 130 and 140 respectively, with the necessary changes as will be disclosed herein. The method starts with steps 210, 212 and 214 that receive the input data for the current plant analysis.

Step 210, similar to step 110, receives one or more macro photography images of a Cannabaceae plant. Step 214 receives other photography images having a pixel size greater than 100 um×100 um, hence potentially having a larger field of view that enables capturing a larger portion of the plant or even a full image of the whole plant.

Step 212 receives additional information such as the location the images were taken, the date & time the images were taken, the data inputting user name, ID and type (e.g., farmers, growers, producers, cultivators wholesalers, retailers, end consumers, and the like). For example if the data is uploaded by a specific cultivator the strain type of the plant might be deduced with 100% certainty without performing an analysis. If the data uploaded by a wholesaler, retailer or end customer, the name (or ID) of the previous link in the distribution chain and the commercial name of the product may give additional important information that can assist and improve the analysis.

The type of photography imager and optics may also be entered into the auxiliary data as well as any other data that can be helpful in one way or another to characterize the plants or the plant products.

All the input data are forward to step 250. Step 250 (analysis manager and input preprocessing) decides based on the input data which further steps will be performed.

Some preprocessing of the data, may be performed if necessary, for example a montage may be made from a plurality of images.

Step 250 stores the input data in the database. Step 250 may also fetch some data from database 260 and use it in the current analysis. For example, data from the same growers, with a previous date, may be fetched for performing comparative analysis.

Step 250 forwards the image data to a two-stage classifier: step 252 and 254. Step 252 is a filtering step that filters out all image data that is not valid images of Cannabaceae plants. These may be images of other plants, images that are taken by accident and can be fabrics, panoramic views and the like. It can also be, as frequently happens, an image of Cannabaceae plants that was captured out of optical focus so the blurred image cannot be used in the analysis.

After the filtering step there is a step of classifying the type of plant that is under analysis. The classification is at least in one level from a general four layer classifier. First, the plant's genus, e.g., Cannabis is determined. Second, the species, such as Cannabis sativa, Cannabis indica, and the like is determined. Then the strain is determined and finally if applicable the phenotype is determined.

The next step in the method is the analysis. The analysis contains three different analysis steps: step 220, step 230 and step 225. Step 220, trichome feature extraction, is similar to step 120. Step 230, is neural network analysis, which is similar to step 130. However in step 230 other input data such as the non-macro photography images and the auxiliary data may be used as additional inputs to the neural networks. Step 225, auxiliary analysis includes all other image and digital analysis on the data that is used to assist with the overall assessment of the plant. It may be image processing of the non-macro images which detect pests, such as fungi, insects, mold, slugs and the like.

As in method 100, the final assessment is done in step 240, which is similar to step 140 but now may contain additional calculations and extended assessment of the plant. The final assessment is stored in database 260. The assessment results are stored in a way that any assessment can fetch the input data it is relied on.

Step 270 is the training subsystem that runs in the background and optionally, runs offline. The training subsystem fetches the data from database 260 and uses this data from time to time to update the neural networks coefficients (illustrated in the figure by a dashed arrow between training subsystem 270 and analysis 230). Optionally, training subsystem can update any models, rule based variables and algorithms used in steps 220 and 225, 252, 254.

In an exemplary embodiment of the invention, the data from classifier 254 is used to assist the trichome feature extraction (illustrated in the figure by a dashed arrow between step 254 and analysis 220). Optionally, the classification data selects different subsets of the neural network in step 230 and assist the analysis of step 225.

In an exemplary embodiment of the invention, auxiliary analysis 225 uses data from database 260 (illustrated in the figure by a dashed arrow between database 260 and auxiliary analysis 225). For example, to determine the maturity of the plant, auxiliary analysis 225 may use the history of assessment of the specific plant as well as other plants that are correlated with the specific plant, for example in the same geographical area, same grower and the like.

Optionally, steps 220, step 230 and step 240 may use the data in the database to assist their analysis (for figure clarity reasons the dashed line to illustrate this relationship was not drawn).

In an exemplary embodiment of the invention, the method performs averaging across different location of the Cannabis flower. APIs in Cannabis are concentrated mainly in trichomes, which are visible for the capturing device. Some areas of a flower may be much more abundant in trichomes than others, to the extent that analyses performed on such variable areas may vary as well.

In one exemplary embodiment of the invention, the Cannabis flower is ground to a powder; the mixing up of all different parts of the flower evens-out the heterogeneity.

To perform the averaging, the training subsystem 270 uses the smallest possible sample weight allowed by the lab. As little as a 100 mg sample weight may be used, or even a single trichome can be analyzed.

In some cases, the imaged material is split between two labs to get optimal performance so 200 mg samples are used. The analysis is performed by having a batch of a plurality of images taken from different areas of the plant sample. Each image is analyzed in the system, gets its own result, then all the results from that batch are averaged, to give a general result for the entire batch.

In an exemplary embodiment of the invention, the batch imaging is performed using a video of the plant, in this case the method separates the video into still frames, and selects a few (typically 3-100) representative frames (filter out blurry/unfocused/otherwise faulty frames) to form the images.

In an exemplary embodiment of the invention, the method uses 3D reconstruction or other spatial relative location detection methods to make sure the selected frames from the video are indeed from different parts of the plant, and possibly chooses the images from specific pre-configured areas.

In an exemplary embodiment of the invention, machine vision (elements 220,225,230) is performed as follows: Each photo received from the user by the system is checked for the existence of several organs/organelles/organisms and their characteristics, including plant and other phenotypes. The checking procedure may be fully or partially automatic.

The general scheme of such a check is detection of phenomena (e.g., features, or a combination thereof) distinctive to targeted organs/organelles/organisms using image analysis (e.g., machine/deep learning) software, comprising of one or several algorithms, each designed to detect a different target.

If such target is found in an image, it may be segmented ("extracted", i.e. using object detection techniques)—i.e., isolated as a Region Of Interest (hereinafter, ROI) out of the entire image. Such ROIs can then be classified and measured for different characteristics (such as abundance, size, shape, color and more).

Alternatively, the images are analyzed without the use of ROIs, but by detection of certain metrics from the large parts or the entire image (e.g., coloration), or that the segmentation process is done concurrently by the same algorithm used for the target detection, or some combination thereof.

Herein below is a list of examples of different targets and possible versions of algorithm based feature extraction, none, all or any subset of which may be provided by the proposed system.

Example implementations for each are described below:

Maturity—determined by trichome (density, shape, size, color), pistils (color and shape), and flower total appearance (bud "density").

Potency—same as maturity. Can be done on "fresh" (in cultivation) or "dry" (post-harvest) flowers. Using such examples discussed in the maturity feature depicted above. Dataset is built so that each image has a corresponding total THC value obtained from testing the photographed plant in recognized test systems such as HPLC-MS labs.

Mold—*Botrytis cinerea* (Bc) (early—hyphae and spores, late—brown spots), Powdery mildew (white coloration on leaves and flowers).

Insects/pests—Acari (mites themselves, the webbing, secretions, larvae), aphid (aphid themselves, the webbing, secretions, larvae), arthropods herbivory marks.

Nutrient—coloration of leaves.

Turgor—physical appearance of leaves.

Growth rate/direction—by continuous plant tracking (possibly a "time-lapse" like data).

Sexing—axillary bud detection in the first maturation phase of the plant. There is a distinct difference of that area (between male and female plants) which is distinctive of the plant's sex.

Phenotyping—appreciating leaf and flower coloration and trichome shape, color, size and density. Important for breeders.

Dry—by leaf color, flower volume, trichome shape, color, size and density.

Cure—by leaf color, flower volume, trichome shape, color, size and density and more specifically dynamic changes in the size of the trichome head (capitates).

Storing/purchase tests—these checks are a combination of one or more of the above checks, e.g., to check if the flower is infected with mold AND if it is cured properly etc.

In an exemplary embodiment of the invention, machine vision learning algorithms are provided.

The detection of features distinctive of targeted phenomena (e.g., pathogen, organelle) may be achieved by machine learning methods such as deep learning and neural networks.

For each phenomena, targeted as biologically relevant, a separate algorithm is developed, e.g., an algorithm for detection spider mites and another algorithm for detection of *Botrytis cinerea* hyphae.

The learning algorithms may be used with human (or otherwise) classified data.

For example, 10,000 images (2D or 3D) that are classified as containing a spider mite may be used as an algorithm training dataset (while comparing to similar photos classified as not containing spider mite).

The learning methodology may output an algorithm that detects visual aspects distinctive of that spider mite (in this example), which may even be (but not limited to) a combination of shape, color, and relation to other aspects of the image (different visual elements on one hand, and metadata such as date and geography on the other hand).

To enable this leaning algorithm methodology the following operations are performed:

Manual/semi-manual classification/usage of a pre-classified images indicating what is apparent in them, such as organelles, organisms, and other biologically relevant phenomena (e.g., spider mites).

The classification may be in text describing the existence of the phenomena and/or by marking the location and outline of the phenomena and/or by documenting quantitative characteristics of the phenomena (such as color hue, size, certainty of classification accuracy).

1. Learning methodology with a training set and a test (validation) set may be used.
2. Continuous iterations may be done, until the algorithm is refined and robust, while avoiding over-fitting and minimizing under-fitting.
3. Continuous refinement of the algorithm may be done, by implementation of feedback from the ecosystem of other algorithms developed for other phenomena, and of user and other feedbacks as to the accuracy of the algorithm (e.g. from user feedback and from the service provider's inner company feedback).

In an exemplary embodiment of the invention, the one or more of the following Cannabaceae plant characterizations and assessments are performed:

1. Assessing maturity
2. Detection of mold
3. Detection of insects and pests
4. Detection of nutrient deficiencies and excesses by leaf colors
5. Detection of turgor (water pressure) by plant shape
6. Detection of growth rate/direction by plant shape and movement over time
7. Assessing plant gender/sex organs
8. Phenotyping support (for breeders)
9. Assist in flower drying
10. Assist in flower curing
11. Assist in flower storing
12. Assessment of flowers' APIs such as Cannabinoid, terpene or flavonoid concentrations e.g., Tetra-hydro-Cannabinol (THC), Cannabidiol (CBD), and Cannabinol (CBN)
13. Purchase testing—including potency and safety (mold, insects). Optionally can be used in an automated purchase testing system such as an e-commerce setting.

In an exemplary embodiment of the invention, the assessment of maturity; detection of mold, insects and pests; assessing plant gender; phenotyping support; assist in flower drying, curing and storing; assessment of APIs concentrations and purchase testing is provided, using macro photography images.

In an exemplary embodiment of the invention, detection of mold and other diseases, insects and pests is provided.

Each pathogen may be checked for by using the feature extraction method depicted above, only instead of detecting spheres to locate trichomes, a unique shape detection tool is used for each pathogen, based its actual shape in the real world.

For example, an initial infection by *Botrytis cinerea* looks in macro photographic image as white lines with sharp angles, and no apparent unified direction, reaching lengths of 10 to hundreds of micrometers.

Early infections by *Alternaria* spp. and *Cladosporium* spp. causing a "sooty mold" look in macro photographic image as black spots, reaching length of 10 micrometers to centimeters.

Aphids look in macro photographic image like white, yellow, black, brown, red or pink insects in the scale of millimeters.

In an exemplary embodiment of the invention, nutrient deficiencies and excesses assessment is provided. Some nutrient deficiencies and excesses in plants such as but not limited to *Cannabis*, cause color changes on the plant's fan leaves to the extent human inspection of these leaves lead to a successful diagnosis. Although the mechanism of the color change is not fully known it is a well experienced method used by seasoned agronomists.

The image processing protocol for extracting the leaf coloration pattern comprises feature extraction methods to detect the entire fan leaf (by shape, maybe by color as well) and then spatially fragmenting the detected leaf region into separate ROIs.

The ROIs in each leaf is measured for color and the color differentiation profile between the different parts of the leaf is given a grade (e.g., a leaf with yellow tips may be marked as C while a homogenously green leaf may receive the mark A).

Taking other data into account (such as the leaf location on the plant, the plant age and maturity, environmental conditions etc.) the calculated marks of different leaves in a plant helps determine the nutrient deficiency/excess of that plant.

In an exemplary embodiment of the invention, the system or method assesses the turgor, growth rate and growth direction. By continuous measuring of the angle of the main and minor stems and fan leaves of the plant the system learns about the curvature of the plant which leads to conclusions regarding water tension (turgor). Adding the angular data to continuous volumetric assessments (by using 3D imaging or other methods) leads to assessment of growth rate and growth direction.

In an exemplary embodiment of the invention, the system or method detects gender/sex of the plants. In the early flowering stage of the *Cannabis* plant (and other Cannabaceae plants) there is a clear physiological difference between the male and female organs (in the scale of millimeters). By means of feature extraction (as discussed above, with or without using 3D) the organs can be detected and differentiated.

In an exemplary embodiment of the invention, the system or method assesses phenotypes. In cultivation of certain plants such as *Cannabis*, breeders seek to increase potency and yield of plants by cross breeding two parent plants, and screen the resulting offspring.

In *Cannabis* for example, image analysis with the current invention enables the users to assess the density and spatial location of trichomes in the offspring's flowers (i.e., the relevant phenotype), and in that manner assist the breeder in giving a specific score to that offspring, reflecting their attractiveness for further cultivation.

In an exemplary embodiment of the invention, the system or method assesses Cannabaceae plants products characteristics during drying, curing, storing and selling phase the producers for cultivators, traders, wholesalers, retailers and the like.

The system checks for change in stalked-capitate trichomes' "head" (sphere) diameter, since it was shown to change with the curing process. Alongside microscopic observations, macro-scale (centimeters) observation of the cut flower (bud) can be used to inspect the change in its total volume and coloration change in the shades of green. This visual data can be accompanied by relative humidity (RH) data the user has regarding the bud in question, days into process, reported smell changes and more.

In an exemplary embodiment of the invention, the system or method analysis includes receiving, processing, modeling and analyzing 3D images. While a single image of a captured location may contain a lot of information, it may be of necessity to use 3D reconstruction methods by the means of stereophotogrammetry, which involves taking several images of the approx. same location from different positions.

Alternatively, a user creates a short video or a sequence of images taken in short intervals (10 images per second for example, in "burst mode"), while moving the camera (pan, tilt, close in, back up etc.), creating consecutive frames with multiple points of view for the same location of the plant/plant tissue (this technique can be done with or without magnification). The slight differences in point of view of images of the same location, while still keeping identifiable common points on each image, allows a 3d reconstruction by principles such as parallax, triangulation, minimal reprojection errors, and minimal photometric error (the latter refers to non-specific feature-based method, also called direct method, which uses intensity differences).

There are software applications that perform such single camera 3D reconstruction (also known as monocular 3D reconstruction, and Structure from Motion or SfM), for example: Meshlab, VisualFSM.

The analysis method of the current invention may utilize one of the above mentioned software or may use a specifically developed application.

The 3D model of the plant (or the plant tissue) is used to perform 3D feature extraction with improved photogrammetry capabilities such as trichome volume (when modeling from micrographs), leaf relative size and positioning on the entire plant (when modeling from non-magnified images of the plant).

In an exemplary embodiment of the invention, the assessment is qualitative (for example, assessment or detection of pest).

In an exemplary embodiment of the invention, the assessment is quantitative (for example, assessment of maturity level or THC concentration).

In an exemplary embodiment of the invention, the assessment is followed by suggestions for action.

Maturity diagnosis is both qualitative, and upon reaching a certain threshold (for example, 100% maturity), suggestion for harvest is reported. The threshold can be set based on the service provider's knowledge base or upon the user's input. That threshold for harvest which leads to a suggestion for action is an example for a rule—a combination of a detected plant condition and a suggested action. For example, for maturity the rule can be "when the detected flower is 100% mature—harvest it". The service provider knowledge base or the user preferences may also determine the plant condition which may be set as the threshold condition.

Figure 4:
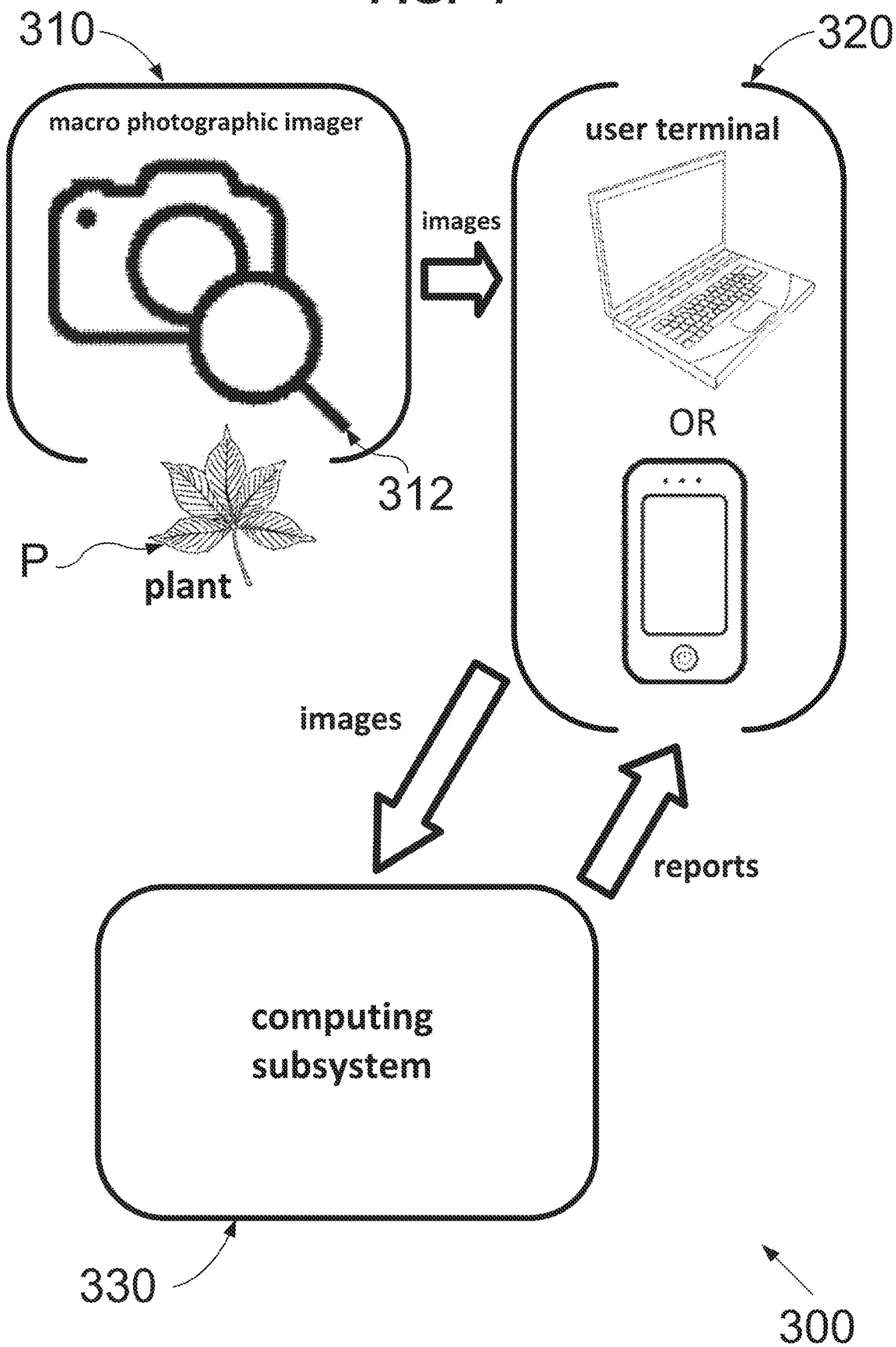
FIG. 4 is a conceptual block diagram of a system for characterization of Cannabaceae plants.

Reference is now made to FIG. 4. FIG. 4 illustrates a conceptual block diagram of a system for characterization of Cannabaceae plants. The system, 300, comprises: one or more macro photographic imager 310; one or more user terminals 320, receiving images data from the one or more macro photographic imager; and a computing subsystem 330 comprising one or more processors.

Macro photographic imager 310 takes images of the Cannabaceae plants P. Macro photographic imager 310 may comprise a separate optical device 312 such as a lens, or a lens that contains an integrated light source or the like. Macro photographic imager 310 may be a camera, a webcam, a macro-shooting capable camera, a professional DSLR camera with a macro lens, a smartphone, a smartphone mounted with an accessory magnifying lens (typically 10-40× magnification is used), a capable of image taking binocular or microscope.

Optical device 312 may be a hand-held magnifying glass (such as a jeweler's loupe) manually held inside the optical path between a camera and a plant P. In an exemplary embodiment of the invention, optical device 312 is a lens and holder designated to be attached to certain cameras, including smartphones. For the trichome analysis, the magnification should provide a pixel size smaller the 100 um×100 um.

User terminals 320 preferably contain an interface to receive the images from macro photographic imager 310. User terminal contains input and output devices to command and control the system, for example to initiate an image taking, and to present the reports of the computing subsystem to the user.

The user may be farmers, growers, producers, cultivators wholesalers, retailers, end consumers and the like. In an exemplary embodiment of the invention, user terminal 320 comprises email application for sending the image from a computer or a smartphone to computing subsystem 330 resides on the cloud. Alternatively, a dedicated software application running on the user terminal 320 is used to transmit the images to a computing subsystem 330. In specific, the dedicated software application may be a smartphone app running in a native iOS/android/windows/Linux/other a native OS for smartphones.

Computing subsystem 330 preferably comprises one or more processors and communication links having wire or wireless interfaces to receive the images from user terminals 320. In an exemplary embodiment of the invention, computing subsystem 330 comprises remote processors and the communication between user terminals 320 and the processors is performed using a network, in general, and the Internet in specific.

The interface of user terminal 320 to the communication link, e.g., the network, may include cellular protocols, such as GSM, CDMA2000, 3G, 4G, or the like, LAN protocol such as WiFi, Ethernet or the like, and PAN protocols such as Bluetooth, NFC or the like. In an exemplary embodiment of the invention, computing subsystem 330 comprises a server farm resides in characterization of Cannabaceae plants service provider's premises. Alternatively, computing subsystem 330 is a cloud computing service. In an exemplary embodiment of the invention, computing subsystem 330 is implemented as part of the user terminal. For example, a smart phone with macro capable camera may implement system 300 in full, wherein macro photographic imager 310, user terminal 320, and computing subsystem 330 are all implemented on the same device. Yet in another exemplary embodiment of the invention, the macro photographic imager 310 is a professional DSLR with macro lens and WiFi modem, user terminal 320, and computing subsystem 330 are both implemented in a personal computer (PC) resides in the user's premises. The PC comprises WiFi modem to capture the images immediately after they are taken. Alternatively, the images are stored in the camera storage and uploaded using interface such as USB to the PC.

Figure 5:
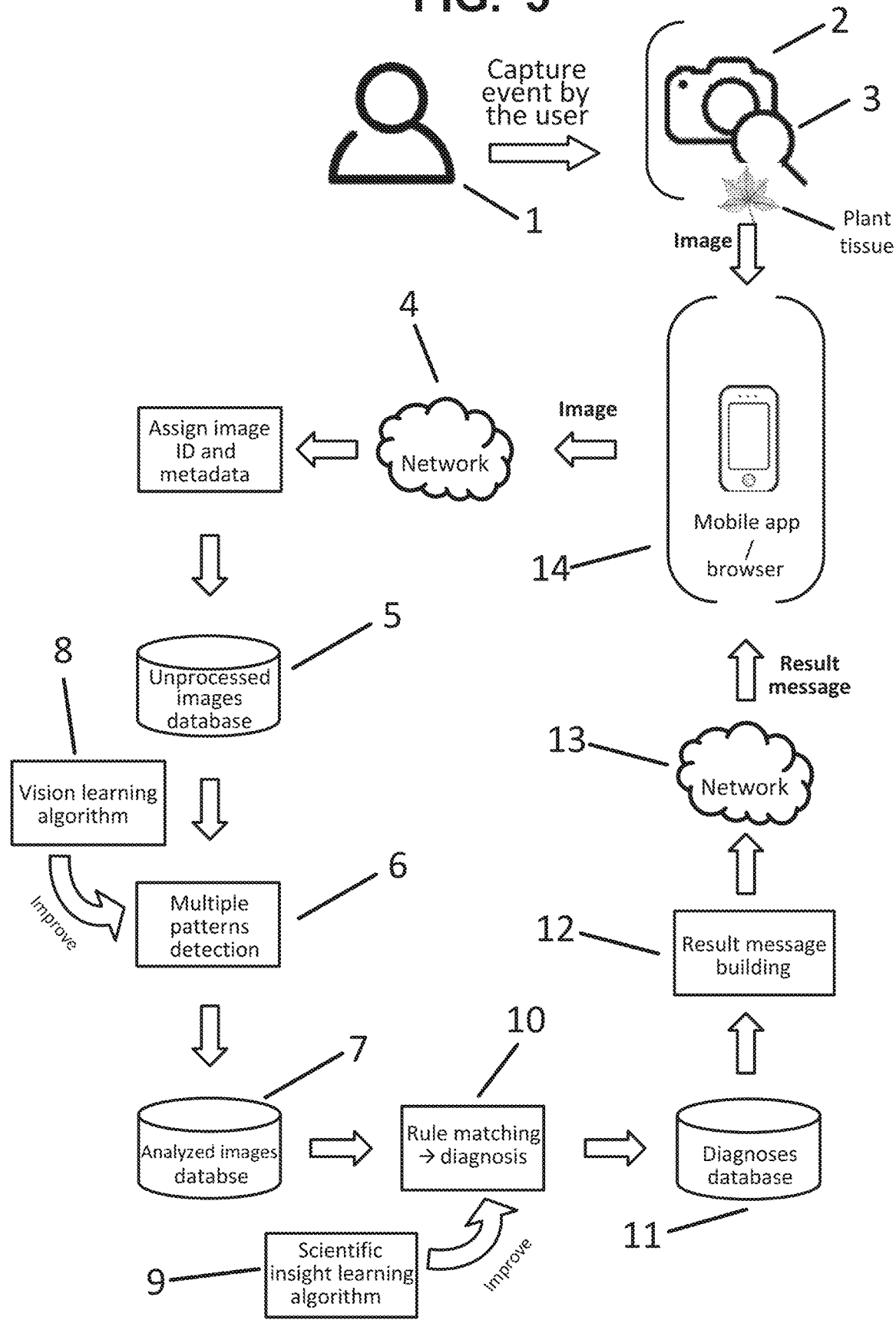
FIG. 5 illustrates a mixed flow chart and block diagram of an exemplary embodiment of the invention.

Reference is now made to FIG. 5. FIG. 5 illustrates a mixed flow and block diagram of an exemplary embodiment of the invention.

The diagram contains the following elements: A user 1, a camera 2 comprising memory space to store images taken by the user, An optional magnifying lens 3 attached to the camera 2, A communication link 4 for transferring the images to the computing subsystem, a database 5 of unprocessed images and metadata of corresponding image, a machine vision algorithm 6 (e.g., image processing algorithm), a database 7 of vision algorithm 6 output and metadata, a data mining learning algorithm 8 for improving the vision algorithm, an optional data mining learning algorithm 9 for improving the rules for achieving a diagnosis, a rule set—output diagnosis 10, a diagnoses database 11, a formatter 12 that convert the diagnosis into a result message, a communication link 13 for transmitting the decision back to user 1, and user terminal 14 that transfer the images from camera 2 to the communication link 4 and present the result massage to user 1. The elements of the FIG. 5 diagram are now described in more detail, in accordance with exemplary embodiments of the invention.

User 1 is a cultivator/vendor/customer that need the assessment of the Cannabaceae plants or its processed products.

Camera 2 (i.e., macro photographic imager) may for example comprise: an amateur digital (or film) camera, a web-cam, a macro-shooting capable camera, a professional DSLR camera with a macro lens, a smartphone, a smartphone mounted with a magnifying lens (2-100× magnification), a binocular, or a microscope. Camera 2 has memory, for example camera's memory card. The images stored in the memory is transferred to a personal computer (PC), alternatively, a printed image is scanned and stored into the PC. The image data may be transferred from the macro photographic imager to the PC memory space (or to a smartphone memory space) by a cable or by wireless communication link.

Magnifying lens 3 may be a hand-held magnifying glass (such as a jeweler's loupe) manually held inside the optical path between the camera and the plant tissue.

Alternatively, a hard-wired lens which is a part of a camera 2 may be used. Yet another option is having a lens and a holder which is designated to be attached to camera 2.

In an exemplary embodiment of the invention, a camera is connected to or integrated into, a microscope, replacing the camera 2-lens 3 pair in the system.

For the characterization of Cannabaceae plants that include the extracting of the information related to trichomes, the magnification should provide an appropriate image resolution to detect these organelles (which are typically 100-500 um long, 25-100 um wide).

In order to capture as many of these organelles as possible, as large as possible field of view and depth of field is preferred. In order to resolve these organelles the 'pixel size' (the size of an object in the real world, represented by each pixel) should preferably not be over 100 um×100 um, but in order to capture as much organelles as possible, the field of view size should preferably not be smaller than 1 mm×1 mm. This may necessitate special optics, elaborated hereinafter.

Communication link 4 may be an email service for sending the images from a PC/smartphone and other possible user terminals. Alternatively, communication link 4 may be a cloud sharing folder on user terminal 14 devices, or a browser based SaaS service. A dedicated software or smartphone app that is in connection with the computing subsystem is yet another option. Such dedicated smartphone app may be a native iOS/android/windows/Linux/other native OS for smartphone, or a cross-platform based app. The app may be developed using tools or platforms like Cordoba and Adobe PhoneGap Developer. The said app may connect with the service provider's server through IP, TCP/IP, http, https or JSON protocols.

Database 5. Memory, stores all unprocessed images, including all data collected at the capture event (plant identity, time, geographical data, environmental and internal conditions) and other data concerning the image (such as user credentials). Database 5 may be any SQL based database (e.g., MySQL) or non-SQL database (e.g., Cassandra, MongoDB).

Machine vision algorithm 6 is a computer software code running on the computing subsystem; the software transforms the visual data of the received images into meaningful metrics. One analysis option is to perform color based classification. Another option is to do feature extraction by shape (e.g., trichomes' round head, mold's webbings' straight lines), each of which is later measured for different parameters (e.g., color, shape, diameter, size, volume).

Optionally, Machine vision algorithm 6 is implemented by applying machine learning, deep learning (e.g., using neural networks). Such a learning algorithm can be constructed by training (and validation/test) of datasets containing pairs of images (similar to images used as input to the analysis algorithm).

The values correlated with those images, depend on the diagnostics features (e.g., total THC concentration, mite species, maturation and the like). In an exemplary embodiment of the invention, the algorithms improve over time by getting user/internal feedback.

Such user feedback can be comprised of user rating as to their perceived quality of the diagnostics they received, metadata provided automatically from the capturing/transmission device (e.g., time, location) or manually by the user (e.g., name of strain), by user inputted organoleptic data (e.g., smell), or by user decision making (e.g., chosen course of action in light of a given diagnosis, either entered manually or by choosing the solution offered by the app, leveraging the wisdom of the crowd).

The machine vision algorithm may be a tensorflow python graph file (.pb), .h5, .hdf5, or other format used for neural nets architecture and weights storage. The algorithms may also be written in other languages/libraries such as PyTorch, Caffe, and others. The neural networks weights are set through a process of back-propagation to minimize a loss function, through iterations on a training set, with a control against over- and under-fitting with a non-congruent validation set.

In an exemplary embodiment of the invention, the programming language and libraries are installed directly on the computing subsystem server or in a virtual machine/cloud environment. The server may be a physical computer belonging to (or rented by) the service provider or may be a "cloud" instance with no specific allocated machine at all times. The machine vision algorithm (and other components of the system) may be all on the user's computation device (e.g., a smartphone) with the inference and result reporting done locally in the user's machine.

In an exemplary embodiment of the invention, the machine vision algorithm can actually be composed of several similar algorithms as disclosed hereinafter. A typical example for a structure for such algorithm hierarchy for *Cannabis* THC detection is: first classify if the image contains a *Cannabis* plant or not. If it is classified as containing *Cannabis*, then the image is classified into a subgroup of species/strains/phenotypes. In that subgroup, a specific THC concentration regression model is applied to detect the final result.

Database 7 stores the data derived from each image (depend on the parameters, the algorithm 6 is set to measure) and additional metadata from database 5. Database 7 may be an SQL based database (e.g., MySQL) or non-SQL database (e.g., Cassandra, MongoDB).

Data mining learning algorithm 8 is based on a learning set of manually classified images (not illustrated in the figure), the improved vision algorithm may be improved by utilizing methods of machine learning. Continuous product development efforts of the service provider is a way to obtain growing, high quality data needed for the quality of the analysis provided by algorithm 6.

Data mining learning algorithm 9 takes into account the entire data gathered, including some not elaborated upon above (such as chemical analysis of flower previously photographed). A learning technique (such as deep learning, neural networks and more) may be utilized to find new unforeseen connections between different levels of data regarding each flower and the latter's status. This section regards the continuous product development efforts for improving algorithm 10.

Rule set—output diagnosis 10 is the step of calculating and reporting. The rule set is a list of pre-defined conditions and the matching diagnosis that arise from passing them.

The rules and diagnoses matching can be determined by the service provider or the user 1. For example, a set of rules can be:

1. IF 30% of captured trichomes are 70% brown THEN the diagnosis is: "Harvest ready".
2. IF mold is detected with 99.99% accuracy THEN the diagnosis is: "Mold detected".
3. IF both (a) and (b) occur, the diagnosis is the same as (b).
4. IF mold is not detected with over 10% THEN the diagnosis is; "Mold not detected".
5. IF (4) is true and the total THC is larger than 20% THEN buy the product. After being checked to pass each of the rules in the set, the diagnosis regarding that image is achieved.

Diagnoses database 11 stores all diagnoses, linked to their counterpart images in databases 5 and 7. Diagnoses database 11 may be an SQL based database (e.g., MySQL) or non-SQL database (e.g., Cassandra, MongoDB).

Formatter 12 generates a result message. The message may be formulated as text and/or a graphical message (e.g., plot, drawing, photo, video animation and the like). The message may be intended to be a decision support tool. An exemplary massage for the cases discussed above may be the following:

1. "This plant/flower is ready for harvest".
   Another possible answer:
   "Harvest is due in 13 days".
2. "This sample contains mold with 99.99% certainty".
3. "It is not advised to harvest this flower as it is potentially toxic, contains mold".
4. "No mold detected" (or, in this case, the system may not report any message).
5. "This product is in good quality, you can purchase it".

Communication link 13 may be the same link as communication link 4. Alternatively it can be a different link. In an exemplary embodiment of the invention, communication link 13 is the Internet. The link transfers back to user 1 a written (text) and/or graphical messages conveying the result message depicted in 12. In the case of a smartphone app, the messages may be transmitted from the service provider's server through IP, TCP/IP, http, https, or JSON protocol.

User terminal 14 comprises input devices like touch screen, keyboard, mouse and the like. User terminal 14 comprises output devices like display, speakerphone and the like. In an exemplary embodiment of the invention, the user terminal 14 is a smartphone, a tablet, a laptop, a dedicated hand held terminal or the like. In an exemplary embodiment of the invention, the user terminal is a stationary terminal such as a desktop computer, a workstation or the like.

In an exemplary embodiment of the invention, a plurality of imaging is performed one image at a time wherein user terminal 14 displays a user interface with some guidance to the user regarding which areas to capture images of next, and when the number of images is sufficient to obtain a reliable diagnosis.

Figure 6:
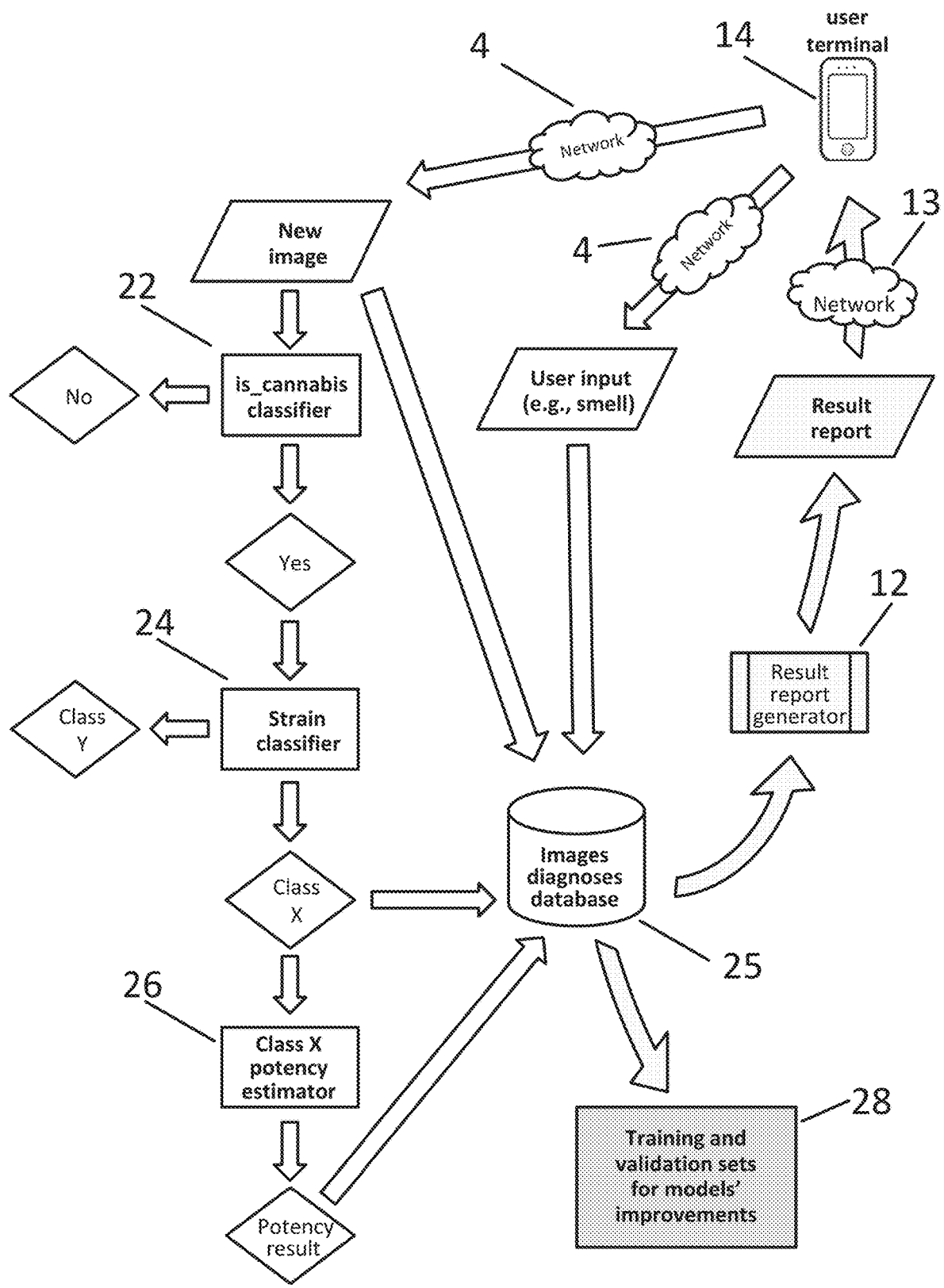
FIG. 6 is a mixed flow and block diagram of another exemplary embodiment of the invention.

Reference is now made to FIG. 6. FIG. 6 illustrates a mixed flow and block diagram of another exemplary embodiment of the invention. In this exemplary embodiment of the invention a potency analysis of *Cannabis* plants or *Cannabis* products are disclosed. Potency analysis (e.g., THC concentration) is one of the applications of this invention. The chemical test is not limited to dry *Cannabis* flowers, but also to fresh flower, and concentrates.

Specifically it may be applied on certain kinds of hash (e.g., live resin/rosin, isolator, bubble-hash and other concentrated that keep the trichomes structure intact). These products are made out of condensed trichomes, which can be detected by the system's algorithms. It may also be applied onto concentrates that do not preserve the trichome head structure, with the aid of a white-balance calibration apparatus to appear in the same frame as the concentrate.

The system or method of FIG. 6 comprises user terminal 14 and communication link 4 and 13 similar to elements 14, 4 and 13 disclosed in FIG. 5 and their companion description hereinabove. User terminal 14 is operated by user 1 and comprises camera 2 and magnifying lens 3 (not shown in the figure). Database 25 is a unified database (replacing databases 5, 7 and 11 of the embodiment illustrated in FIG. 5) that stores the images the user sent as well as the analysis products and the final report. Optionally, the video combine macro (zoom in) and normal (no zoom in) images to get better context and therefore improved results.

After the one or more images are received by the computing subsystem using communication link 4, classifier 22 analyzes the image. Classifier 22 may be a neural network classifier that has been trained to detect Cannabis flower images (standard or macro images). In addition, with the images sent to analysis, user may send auxiliary information such as plant identity, time and location, environmental conditions (temperature, humidity and the like), and subjective data like smell of the plant.

In an exemplary embodiment of the invention, the smell is provided by an artificial nose small apparatus. Artificial nose small apparatus may detect the presence of chemical molecules in the air surrounding the plant. In an exemplary embodiment of the invention, a non-visible spectrum light sensor (spectrometer) may be used to detect additional information on the formation of the sampled material (e.g., UV, NIR).

If an image passed the first "is Cannabis" classifier 22, the analysis of the image continues with analysis of the strain of Cannabis by strain classifier 24. Next this image is analyzed in class X potency estimator 26. A simplified exemplary implementation of class X potency estimator 26 is provided in FIG. 7.

Figure 7:
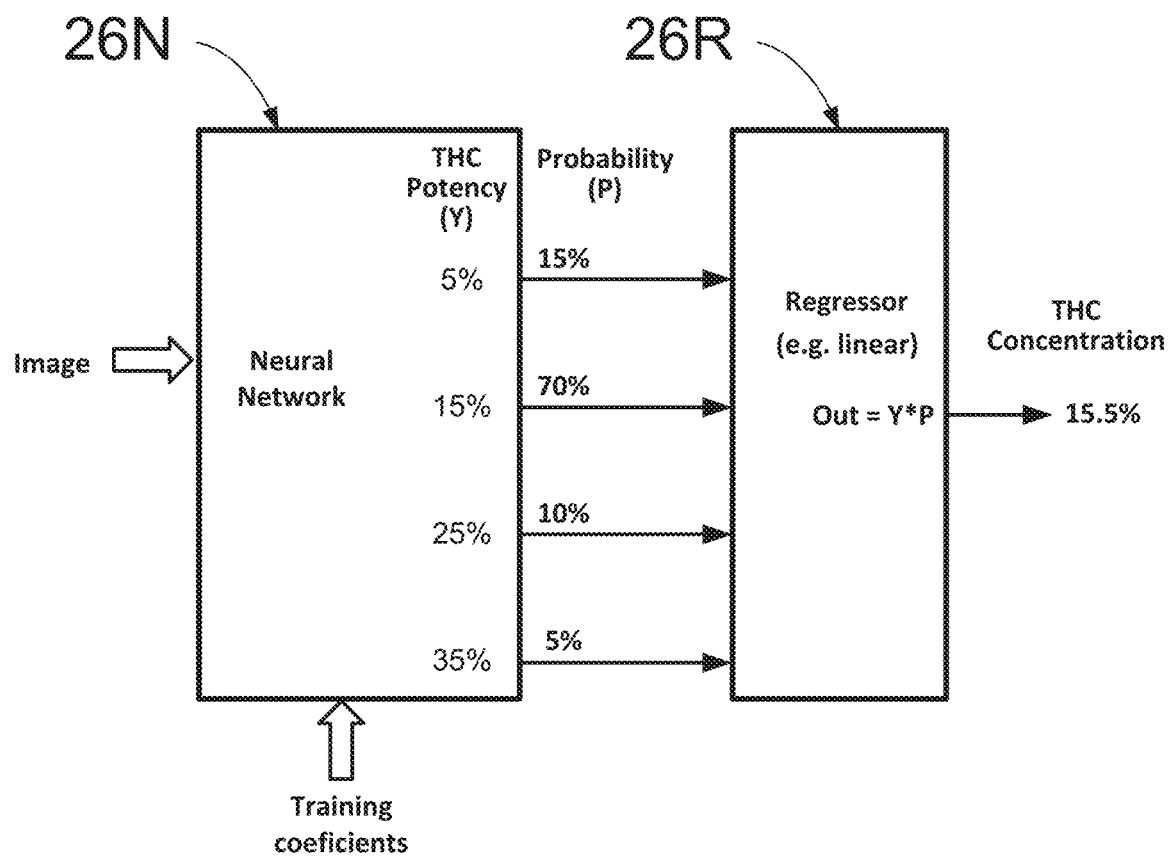
FIG. 7 is a block diagram of a simplified potency estimator.

Reference is now made to FIG. 7. FIG. 7 illustrates a block diagram of a simplified potency estimator. The estimation is performed in two steps: neural network 26N followed by regressor 26R. In this simplified example, the neural network 26N has four outputs and has been trained to detect a specific strain of Cannabis, and four "classes" of THC potency (i.e., THC concentration) have been trained: 5%, 15% and 25% and 35%.

The training of this four output neural network has been performed by taking the image training data set with the corresponding THC concentration lab tests and splitting them into four sets.

The images in which the measured THC concentration is less than 10%, are assigned to the class 5%. The images having a measured THC concentration between 10% and 20% are assigned to the class 15%. The images having a THC concentration between 20% and 30% are assigned to the class 25%. Finally, the images having a THC concentration higher than 30% are assigned to the class 35%. Note that it is a rare event that THC concentration is higher than 40%.

In the training, each set is inserted into a process of back-propagation to minimize a neural network loss function, through iterations on a training set, to set the training coefficients.

The network output is configured in a way that the output for each concentration class is the probability the image is associated to this class, and the overall probability sums to one.

The output of the four probabilities is the input to regressor 26N. The regressor in this case, is a linear regressor.

The THC concentration vector Y is multiplied (inner vector multiply) by the probabilities vector P. The output in this case is THC concentration of 15.5%. In general, the regressor formula may be non-linear and the weight coefficients may not be direct probabilities as in this simple example.

Reference is now made back to FIG. 6. The potency estimation or assessment is stored in database 25. If there are more images associated with the plant, each of these images flows through steps 22, 24 and 26 and the associated estimation product is stored in database 25. When all images are processed, the final result is calculated by considering (e.g., averaging) all estimation products.

Taking a plurality of images and averaging the analysis is recommended because of the inherent variability/heterogeneity of the Cannabis flower, incorporating concentrated potency loci (a.k.a. hotspots).

As the flower is mostly consumed as a large piece (typically about 0.3-2 grams), the user consumes a mix of the hotspots and the weaker spots. It is therefore more meaningful to the user to find out what is the average potency of the flower they are testing—including hotspots and other parts as well.

Therefore a scan of the flower from as many facets and angles as readily possible can be a key to a successful diagnosis. Such a scan can be achieved by taking a set of images (a batch), and sending them as one test to the computing subsystem.

In an exemplary embodiment of the invention, analysis of each image is performed individually, the images' results are averaged, and the averaged result is stored and sent to the user.

Alternatively, the computing subsystem combines the images (the batch) to one image, and processes it in a single analysis pass.

In an exemplary embodiment of the invention, the system is capable of receiving a short video of the flower from all sides, and extracting a plurality of images from this video.

In an exemplary embodiment of the invention, the user terminal 14 (and more specifically, the macro photographic imager 310 in FIG. 4) is a device, into which the plant sample is inserted. The said device is equipped with multiple cameras able to image the sample from several angles, or one camera with a mirror system to allow a photograph to be taken from many angles with one camera. The said device can capture the sampled plant from many angles in a short time and controlled conditions, easing the process of sampling, and can be applied to testing pre-harvest or post-harvest flowers.

When all the analysis product data is saved in database 25, a report generator 12 sends the results to the user terminal 14 using communication link 13.

In this exemplary embodiment only one strain, designated by the name "class X" in the figure is further analyzed.

Alternatively, a multi-strain analyzer may be used. In this case, either a unified analysis algorithm for multiple strains is used, or a specific algorithm for each strain exists in the computing subsystem and the appropriate one is performed based on the classification provided by strain classifier 24.

The data stored in database 25 is used by the training and validation processes 28 disclosed in more details hereinafter.

In an exemplary embodiment of the invention, the system helps the end user with assessment of the consumption dosing for a user. The generation of a potency result together with the user predefined desired dosage, enables the system to provide a suggestion as to how much of the analyzed product to consume.

For example, if the user tests a *Cannabis* flower and it has 20% THC (meaning 200 mg THC per a gram), and the user would like to consume 50 mg of THC in that sitting, for an accurate dosage, the system will suggest weighing 0.25 grams of the product.

This utilization of the invention creates a novel, non-destructive, quick and accurate way to inspect the dose of the actual product and get instructions on how much to consume, in order to get a precise, repeatable medication/recreational effects.

In an exemplary embodiment of the invention, averaging over the entire plant is provided. The closer/more magnified the image is, the lower the probability that the captured image represents the real average of the sample API content (e.g., THC), causing a sampling error and reduction in result repeatability (the chance the user will take another photo of a different area of the same sample and get the same result decreases).

To overcome this problem the user may use a lens with special optic features, specifically a combination of a large field of view and a deep focal depth, while using a high resolution camera sensor.

For example, a field of view of 3 cm×3 cm with a resolution 10 um (pixel size of 10 um*10 um), necessitates only a 9 mega-pixel sensor. The challenge in this case is the optics needed to keep the entire field of view in focus, both because most smartphone lenses cannot provide such a wide field of view at such a high resolution, but mainly because the typical extreme topography of a *Cannabis* flower, necessitating a deep field of view (minimum 1 mm). This optic requirement may be fulfilled either by an optic device supplemented to the image capturing device in the user terminal 14 (e.g., the user's smartphone 14) especially for the service offered by the system; or by some other off-the-shelf relevant optical attachment/capturing device; or without any optical device other than the image capturing device (e.g., the user's smartphone), providing the latter has built-in optic capabilities filling the discussed requirements.

After the user captures this hyper-high resolution image discussed above, the image is sliced to smaller images to be considered a part of one batch. Each image is analyzed on an estimator that was trained on similar small images, and finally all results from that batch are averaged.

Figure 8:
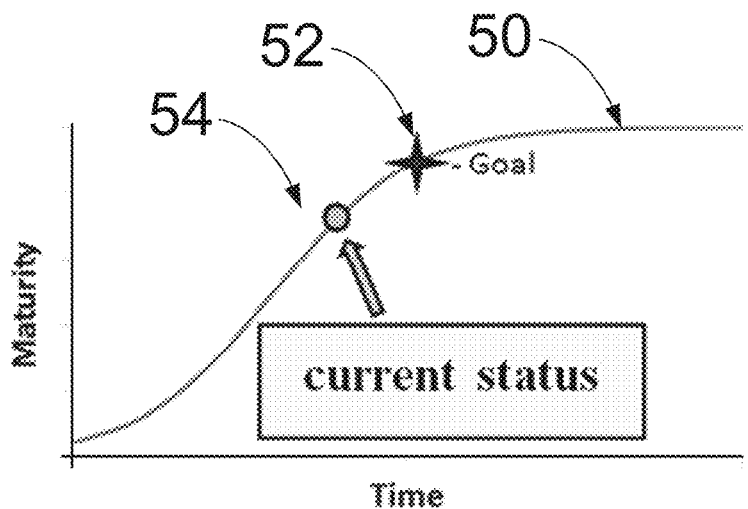
FIG. 8 is a typical maturity vs. time function of *Cannabis* plant.

Reference is now made to FIG. 8. FIG. 8 illustrates a typical maturity vs. time function of a *Cannabis* plant. The function of maturity 50 has an optimal point 52 for harvesting the plant.

One purpose of the method or the system is to assess the current status point 54 in order to recommend to a grower when to harvest. In an exemplary embodiment of the invention, assessment of plant maturity is performed by trichome size, shape, density and color, or other features or combinations thereof.

Color differentiation on the range between white and brown, and also yellow, purple and other colors can be achieved using classic image analysis methods by the means of background subtraction, i.e., removing all pixels which are not brown, white or any light brown colors in between.

The assessment is performed by appointing each remaining pixel with level of "brown" (0 being white) and then calculating the intensity of brown out of the total number of pixels in the background-subtracted image.

An alternative approach is feature extraction, namely picking out the trichomes in each frame and assigning each with an individual region of interest (ROI), with classic image analysis methods or with machine learning methods that may extract more basic features and may build complex connections between these features during the training process.

In an exemplary embodiment of the invention, feature extraction is based on 3D imaging. The feature (for example, a trichome) may be detected by (but not limited to) the distinctive round shape (sphere) of the stalked-capitate trichome head. The round shape (which is otherwise in these scales usually rare) may enable a decisive recognition of the trichome head to establish it as an individual ROI.

These ROIs (whether established thanks to round object detection or not) can be tested for coloration (such as the levels of brown example depicted above), size, shape, density, and more.

In an exemplary embodiment of the invention, the system provides customization for growers with a preferred rule set.

Expert growers have an idea of how a mature flower looks like, in terms of trichome, pistil and over all flower characteristics. In order to empower those expert users and automate the process of evaluation in a way that may be as close as possible to their preferred rules (the visual appearance of the flower as the user wishes to have once the flower has fully matured), the system may ask those users quantitative and qualitative queries that may be used to assess those rules.

Such queries may include the following: "what percentage of clear/white/brown trichomes (each) do you expect to see?", "what should be the color of the pistils?", and "should the flower seem denser and less hairy?" The answers may be quantified and kept in a dataset (table) of diagnosis conditions and the actions fitting to those conditions (the rules dataset). An example for a rule may be: "when there are 50% amber trichomes the plant is a 100% mature harvest the flower".

The expert grower may say that their rule's condition is at a certain measurable metric but have a misconception of the actual appearance of their condition.

Continuing with the example above, the user may say they saw 50% amber trichome when the actual number is 70%. For the system to account for that deviation, the real condition the user is looking for must be found, and not what the users thought or said.

In order to do that a series of photos of trichomes in different plants' maturation stages may be sent to the expert grower with different levels of the condition they are looking for and the expert grower may select the image which they feel is the best representative of their rule's condition.

In the example above, this may be a series of images displaying different levels of amber trichome concentration, and the expert grower may select the photo they feel has 50% amber trichomes. The system may set the number the expert grower chose (70%) as 100% maturity, rather than what the user declared (50%).

In addition, the conditions disclosed above may be set according to scientific or other knowledge accessible to the service provider. The condition may be set according to a certain strain in a certain season under certain growth conditions, based on external knowledge (for example scientific or horticulture literature) or internal knowledge (result of past users' data processing). The internal and external setting conditions may be continuously updated due to the service provider's research. Such research which causes updating of the setting conditions, may be result of growers and cultivators feedback, chemical analysis of plant material upon which a diagnosis was made, and big data analysis by the service provider's supported by machine learning tools. All of these processes are part of the self-improving mechanism and training of the system as illustrated in block 270 in FIG. 3 and block 28 in FIG. 6.

In an exemplary embodiment of the invention, a computerized process, service, platform or system for automated plant diagnostics is provided, based on image analysis of micro- and normal-scale photos, and a decision support automated system enabled by that embodiment. A lot of the metrics used for plant diagnostics are in the small scale, i.e., scale of single millimeters and down. For example, in *Cannabis* cultivation maturity evaluation is based largely on visual inspection of trichomes, small (tens to hundreds of micro-meters in length) hair-like organelles which produce and harbor most of the medical and recreational desired active molecules. In fact, the trichome status can also be used to derive the *Cannabis* flower status after cultivation is over, to monitor flower status through all chains of the *Cannabis* flower industry—dry, cure, store, and purchase (potency and safety) testing.

Phenomena important for any plant cultivator are the initiation of infection of the plant by fungi, viruses and bacteria, as well as nematodes and insects such as mites, aphids and herbivores. Many of these pests and diseases only show macro-scale symptoms days and even weeks after their micro-scale early stages of infection can be apparent through visual magnification. Expert cultivators/agronomists use a magnification apparatus (jeweler's loupe, microscope) and manually check plants to determine their maturity (by evaluating trichomes) and to detect first stages of phytopathological evidence (pests and diseases). Magnification is used for (bulk or consumer) purchase testing. The system illuminates the necessity of the work of an expert, by exploiting the knowledge of the rare, knowledgeable person, who is the only one qualified and responsible for determining health/maturity of the plants. The system solves the problem and limitation in manpower qualified to diagnose plants for health/maturity and enable more checks per plant. In fact, in most cases the expert only has time to check as little as 1 in 20 plants of an industrial cultivation operation, actually performing batch-testing. Beyond cultivation, the lack of fast, low-cost and non-destructive diagnosis for many Cannabaceae plants, such as *Cannabis*, prevents an objective quality assessment needed for adequate pricing. The system disclosed hereinabove provides the need for added checking and testing for every plant, typically enabling everyone who is able shoot a photo of the plant and send it, to receive instant diagnosis.

In an exemplary embodiment of the invention, the system or method assesses maturity curves by repeating acquisition of each location (i.e., plant in general or a more specific location on that plant) as the time passes. Each image and its subsequent analysis contain a timestamp relating to the exact time of acquisition. The results derived from each analysis of each location are organized in a table (or array, matrix or similar data set), and two of the parameters (column values) in this table are the time of acquisition referred to above, and the maturation level (directly or indirectly through metrics such as trichome colors) for that location. Thus for each location a curve can be plotted where the X axis is the time of acquisition (specifically, time in flowering stage calculated by reducing the acquisition timestamp from the user's-report-of-transition-to-flowering-stage timestamp) and Y is the maturity level. For example, it is assumed maturity level is calculated as the percentage of brown/amber trichomes out of all trichomes. In the same way a function can be derived for each location, with X being the time of acquisition and Y the level of maturity. The function may be single to fit all grow stages or may be composed of several sub-functions that correlate to different rates of maturation across the flowering stage. For example of the latter, at the beginning (day 0 and 1) of the flowering phase the maturation level may be 0%, in day 10 of the flowering phase it may increase to 15%, in day 20 to 50%, in day 30 to 90%, and in day 40 (the end of the flowering phase in this example) to 100%. So in this example, the calculated function (and subsequent curve) is a presentation of a (hypothetic) typical dynamic of the rate of the maturation—maturation starts slow, speeds up more and more, then slows down until it reaches a full stop at the end. To enable predictions using this kind of maturation function, the service provider may build in advance (possibly during development) a "model function" of maturation of a typical plant, "the way a plant 'normally' matures", to be regarded as a model of the maturation process, and so to be used to forecast the date in which a certain location may reach a maturity goal (as described above, the goal may be dictated either by the user or the service provider). Different model functions may exist for different plants, strains, growth methods and/or other factors. At any specific time in a user's cultivation, before the cultivation is done, the service provider can overlay the user's actual maturity function of the location in question based on the data the user has sent until that time, and compare the dynamics of that "actual function" of maturity to the model maturity curve. The fit does not have to be (and probably will not be) perfect; the fit between both functions may be in the dynamics, i.e., derivative phase. To continue with the same example as above, the user sends data every day of the flowering stage, and on day 15 a user-data based actual function is created. In this example it is revealed that on days 14-15 the slope of the maturation rate has turned from "a" measured in days 1-2 to 2*a, meaning the derivative of the maturation rate has increased significantly (in this case—doubled), and so the point in time in which the slope has increased to 2*a is determined. This time point where the derivative doubles may (in this example) be assigned as the middle of the flowering stage. In that way, even if the curves don't fit exactly a prediction for harvest is achieved.

For some (not all) phenomena the user may use optical magnification, which can be provided using an off-the-shelf device. The optical magnification device may be a lens attached to a regular smartphone camera, or may contain an internal camera alongside the optic magnification apparatus, in which case the device may be able to be integrated into a smartphone or computer through a USB cable of wirelessly through Wi-Fi, or Bluetooth for example, or be a standalone device that connects to the internet and sends/analyzes the photos without the need for a smartphone/computer. The magnification device may optionally provide some or all of the spatial illumination, light filtration, and specialized focusing. In an exemplary embodiment of the invention, the diagnosis system may potentially be robust enough to derive data from images of the organ in question, shot (imaged) by different cameras, under different lighting, magnification and color balance, providing that they are in a good enough (minimal) focus and resolution. After sending a picture to the diagnosis service provider, the user gets an electronic message (e.g., email, in-app prompt message) with a written or graphical diagnosis based on those images after a few seconds to a few days. Alternatively, the analyses results may be saved on a server, not sent to the user immediately, to be accessed by the user/another user on a dashboard/platform in a SaaS or native software surroundings.

Figure 9:
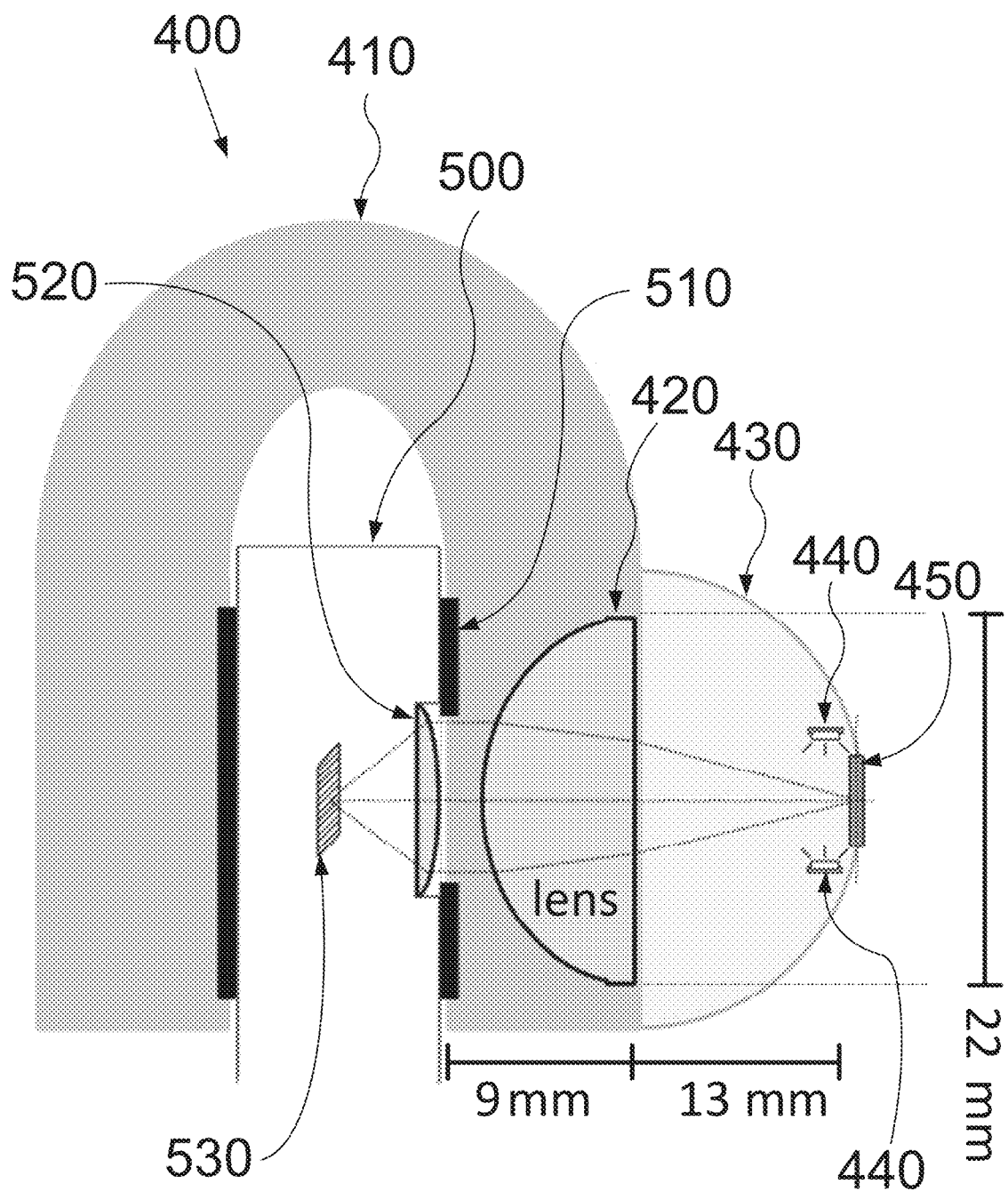
FIG. 9 is a block diagram of an optical magnification device attached to a regular smartphone camera in accordance with an exemplary embodiment of the invention.

Reference is now made to FIG. 9. FIG. 9 is a block diagram of an optical magnification device attached to a regular smartphone camera. The optical magnification device 400 comprises a clip 410, a magnifier lens 420, lighting dome 430, light sources 440, magnifier focal point/plane 450, and an aperture 460 (previously 510). The clip is configured to grip a smart phone 500 comprising phone camera aperture, phone camera lens 520, and phone image detector 530.

The plant tissue is attached to magnifier focal plane 450. In this distance from the phone camera aperture 510 the phone camera image will be in focus. In this example the magnifier aperture/focal point 450 is about 10 mm and the other relevant dimension of the optical system is provided in the figure. Optical magnification device 400 light sources 440 (optional) generate an optimal light to take an image. Light sources 440 are typically LEDS but other light sources including lasers and the like might be used. The magnification of the device illustrated in this figure is about 10×. Other geometries and magnifying lens may provide higher or lower magnification. Digital or optical magnification in the smartphone camera subsystem may be used. Clip 410 is used to hold the optical magnification device 400 to smart phone 500 in such a way that the magnifier lens 420 will be in optical matching with phone camera lens 520 as well as phone camera aperture 510. Phone image detector 530 is typically a CMOS imager but may also be any other camera image sensor technology, such as CCD, used in smartphones.

In an exemplary embodiment of the invention, the system performs better than expert on tasks such as potency testing and harvest timing, to the extent its superhuman performance achieves the task no human can ever fulfill consistently. In these tasks the system allows a chemical analysis of the plant matter to a statistical error of as low as 5%. Better performance is anticipated in the future as more data is gathered. Using a well annotated, high quality, biologically diverse database allows the creation of machine vision algorithms that can measure variety of chemicals.

In another aspect, the proposed system is also much more effective when it comes to home-growers and consumers/medical patients, which are typically less informed than their expert, industrial/retail counterparts. These home-growers/consumers cannot pick (generally speaking) the alternative of summoning an expert to inspect their plants and therefore may benefit greatly from a web based publically accessed platform, which will provide high-quality scientific diagnosis of their plant.

The system also presents a novel usage of the cultivation technique (microscopic inspection), one which is particularly advantageous for non-cultivators seeking to check the status of their plant matter after it has been harvested. In the *Cannabis* flower for example, many processes that occur post-harvest can be crucial for the end-product quality; these are drying, curing, storing, and purchasing—all are of interest to cultivators, vendors ("dispensaries") and consumers. Vendors and consumers may be supported by the system in their effort to check what they are buying prior to and while they are purchasing.

The system disclosed herein above is far superior to that of employing a large number of diagnosticians, because of the cumulative data organization and analysis which it offers. This "data-handling" the solution provides, can enable the sole expert to control each and every plant grown in their facility over a long period of time, or to enable a store owner to have a potency record of all products in stock, through the use a computerized display setting and analysis dashboard, or to enable a store owner to run a potency test on each portion of product sold/bought and set the appropriate price for it on the spot according to the system generated result. This level of data control can transform the abilities of the farmers, grower, expert, trader to reach better, well-founded knowledgeable decisions regarding their crop and the operational side of their facility.

In an exemplary embodiment of the invention, the system provided novel chemistry testing for *Cannabis*. Building on the unique morphology of the *Cannabis* plant, a novel approach to chemical testing is disclosed. As noted above, the accumulation of APIs (mainly Cannabinoids, terpenes and flavonoids) in trichomes, combined with the former's visible coloration and localization within the trichome, allows the system to draw a connection between certain chemicals and the visual appearance of the plant matter. In that perspective, the current invention may serve as a chemical analysis tool used for cultivation, trade, and dosing scenarios. The proposed system can thus be certified to a certain extent as a legitimate chemical testing service, alongside or as an alternative of the existing lab testing, consisting of HPLC/GC/HPLC-MS/GC-MS test equipment and test methods.

In an exemplary embodiment of the invention, the users' information database which may be created as a result of using this system is potentially harboring a lot of value to plant cultivators and consumers, in the form of personalized agronomic suggestions. Relying on the accumulative user data, upon researched agronomic knowledge, and upon user feedback (e.g., of past suggestions produced by the system), the system may be able to use the diagnosis of a user as a basis for a formation of a suggestion to that user, as to how to act upon said diagnosis. Thus, direct personalized recommendations may be provided to users depending on diagnoses the system produced (for example, if the system finds the user's plants are infected by mold a message may be selected (by suitable preconfigured logic) which recommends use of an anti-mold product to that specific user), making the procurement side of the agricultural process more efficient and therefore shorten the lead time of reacting to problems and improve planning. Moreover, the personalized cultivation suggestions may be a lucrative revenue model for the system provider, as it may act as a direct and personalized product marketing/sales/advertisement platform. Such marketed products may be pesticides, herbicides, fungicides, nutrients supplements, nutrient removal products, seeds, clones, service providers (i.e., harvesters), and more.

In an exemplary embodiment of the invention, personalized suggestions is offered to consumers. Basing the diagnosis on the user uploaded image, the system may detect the predicted affect the flower may have on that user (as described in the self-improving feature) and suggest actions to that user. For example, the system may detect the user is analyzing a strain which may have a sedating effect, and thus can warn the user not to plan an activity which demands their full energy. Another example may involve advertisement; say the detected strain enhances appetite, the system may prompt an ad for a food vendor and suggest to the user to order food in advance, so when the food craving is in full swing, their food order will arrive to their door. These suggestions hold a great added value to consumers and may also become a lucrative revenue model.

In an exemplary embodiment of the invention, raising the standards of plant checking to a single-plant checking (and even within the same plant), is practically not feasible with human experts in an industrial context; suggesting that once used to this technology, the users may become dependent upon it. Resembling, for example, the dependency many people have on navigation software nowadays, which is self-perpetuating since many new users do not acquire independent navigation skills. The same goes for home or novice growers which may rely on the system's diagnoses to the extent they may not feel the need to educate themselves on the area of knowledge the system's solution covers. Furthermore, the system serves as backend for a fully automated cultivation/processing system, leaving some of all of the human need for involvement in these processes. For example, automated growing robots (or pods), robotic arms, drones, or other automated systems equipped with cameras, using them to send plant pictures to our system, which sends back a diagnosis to the cultivation system. That automated cultivation system act upon the diagnosis in a fully closed loop automated manner.

Training and Self-Improvement

In an exemplary embodiment of the invention, the system is constantly improved and uses the new acquired data to improve the coefficients of the neural networks and other signal processing algorithms and rules base decision making.

In an exemplary embodiment of the invention, the system use machine learning, deep learning, machine vision, artificial intelligence and the like for the analysis phase.

In order to build the machine vision deep learning model to detect APIs from plant images, in the training phase many high quality images of plants (similar to the images the user can upload later when using the service) are collected. The plants of those images sent to lab testing. The test result with the relevant APIs is used to train the network. The result can be one-dimensional for a network for a specific API, e.g., THC, or multidimensional to train a more complex model able to predict several APIs contents at once.

The following are some thumb roles for a good dataset for the training task for *Cannabis* APIs:
1. The imaged plant samples should be as small as possible (i.e., 100 mg sample is better than 1 gr sample), and this depends on the labs to which the samples are later sent. This will keep this heterogeneity as small as possible.
2. Work with several labs, as current lab testing has its own errors which may change from lab to lab and even between different samples. For the best results, image the plant sample, afterwards grind it up and send it to the different labs (e.g., image a 200 mg plant sample, grind it up and send to two different labs that can each analyze 100 mg samples).
3. Collect samples from as many distinct phenotypes/genotypes as possible. Have several samples from plants across several distinctive spectra (examples here show couples of words standing for the extremes of each spectrum): strong/week, *sativa/indica*, indoor/outdoor, dry/fresh, cured/uncured, etc. To further elucidate, to satisfy the need for diversity of samples across these 5 spectra, one may collect at the least $32=2^5$ different samples.

In an exemplary embodiment of the invention, self-improving in performed as follows: as more users make use of the service the better and faster the image analysis gets; by virtue of suitable learning functionality, pictures uploaded by users will be added to newer iterations of the model training, thus making the model more robust to various use cases, such as different magnifications, resolutions, optical aberrations, lighting, *Cannabis* strains, and more.

Alternatively or additionally, self-improving in performed is done by allowing the users to add input as they use the system to allow a user-generated annotation of the user data. The more data is annotated by users or others, the larger the annotated data becomes and potentially better predictions are possible, and depending on the annotation—the larger the scope of diagnoses becomes. For example, if the user can input the strain name of the plant they are imaging, the image can get the strain-name label, and be a part of a future training/validation set for a model trained to detect strains. Same with smell, if a user can input the smell of the flower being photographed, this makes possible a dataset that can predict the smell of a flower based on its optical appearance, paving the way to predict the chemical content of scent generating compounds like terpenes from visual appearance of a flower. As another example, another input can be the medicinal and/or recreational/psychoactive effect the user experience by consuming the flower used for imaging. This has two main applications—predicting such effects flowers may have from the flowers' images (to generalize the reported effect to other flowers and other users depending on similarities between the original image and the new images used for prediction), or predicting for that specific user how other flowers may affect them (for example if the system detects a user reacts to certain strains in a certain way, the system can notify the user it may experience those effects again if it detects the user analyzes a similar flower). The latter application has to do with the personal decision support system potential of the system, discussed herein above. Further than that, the creation of the database as a scientific record of plant status across a myriad of different conditions may provide insights that cannot be revealed without it, potentially connecting apparently distant facts to meaningful scientific findings and actionable business advice. In summation, some embodiments in the current invention are ever improving and the data it collects becomes more valuable along with the growth in users.

In one example, the training of the THC concentration estimator neural network (see FIG. 7) has been done using two sets of images. The first was 10,000 images of no *Cannabis* case. Those images include: (1) non *Cannabis* plants, (2) fabrics, (3) *Cannabis* images not in focus or other image quality issues. The second set was 10,000 images of *Cannabis* macro photography images that were analyzed by labs. In one optional neural network configuration, the good *Cannabis* images were classified by the ranges of the THC in the lab tests (as shown in FIG. 7) and the network was trained by inputting those images and back propagating the true result to refine the network. In another optional neural network configuration, the neural network is configured to give only one output which is the THC concentration. Yet in another option the neural network is configured to give an assessment of price. Many type of network may be trained for different assessments. The key point for good training is a-priory knowledge of the specific assessment for the images. While in the case of lab test this knowledge is objective, in other cases it may be subjective and depend on an expert assessment. In some neural networks used in this invention the output stage has 1 to 30 outputs (e.g., 4 in FIG. 7), optionally, up to 1000 outputs are used.

The initial training phase is followed by validation (/test) phase. The validation phase performs an additional use of known a-priory images and runs these images on the trained network. If the validation results are not adequate, additional training with improved, data, hyper parameter, architecture or other elements may be pursued. In an exemplary embodiment of the invention, 90% of the known a-priory images are used for training and the other 10% is used for validation, alternatively, 50% to 95% of the known a-priory images are used for training and the other are used for validation.

The network implementation may be a tensorflow python graph file (.pb) (it may also be written in other languages/libraries such as PyTorch, Caffe, and others). The network weights or coefficients has been set through a process of back-propagation to minimize a loss function, through iterations on a training set, with the control against over- and under-fitting with a non-congruent validation set.

In an exemplary embodiment of the invention, databases metadata and training sets for machine learning algorithms leads to new visual parameters that can serve as better indicators to plant status. Since the inception of the service, each image is classified manually or semi-manually, to detect and record the features and meaning every agronomist may see when they use a magnifying glass to diagnose all the phenomena discussed above. Some of the manual classification is done by dedicated employees and some by the uploading users themselves—as assisting information. That way each diagnosis in database can be rated for accuracy, and henceforth the rule matching and pattern detection algorithms can be judged for efficiency. Furthermore, this manual (or semi-manual) classification paves the way for meaningful breakthroughs due to the usage of machine learning tools.

For example, after a sufficient period of time of offering the service, the service provider may accumulate thousands of images of plant maturity tests and the user feedback regarding the diagnosis the initial algorithm proposed. This semi-manually classified dataset can be split into learning and training sets, which may be used to build and train a learning algorithm which may find that there is a better way to diagnose for maturity. For example, the algorithm may find that there is a stronger link between color and maturity when stalked glandular trichome head diameter increases. In an exemplary embodiment of the invention, the database is open to researchers as a source for visual plant data across a myriad of conditions and genetic backgrounds, enabling scientists to explore basic scientific questions, thus potentially paving the way to new findings that can promote agriculture sciences.

Decision Support System

In an exemplary embodiment of the invention, Decision Support System (DSS) is provided. The term DSS means a knowledge-based systems intended to help decision makers compile useful information from a combination of raw data, documents, and personal knowledge, or business models to identify and solve problems and make decisions. In an exemplary embodiment of the invention, the responsibility for choosing the course of action may always be overridden by the grower end user. By adopting the system's suggestions, the grower may automate processes they are already doing, but furthermore the grower may utilize the amount of data that is collected by the system on the plants to reach more educated and learned decisions than growers could have reached without the use of the system. Such automation can serve as the basis for fully automated cultivation/sorting/processing facilities.

An example for such utilization of the accumulated data, is a precise prediction of plant maturity date and therefore harvest timing. By collecting micrographs of individual plants continuously along the growth cycle (about every week) the maturity status calculated by the system at each point can be a basis for calculation of a plant maturity curve (see FIG. 8). This curve is a formula of the maturity process progression up-to-date, added with a trajectory of the predicted maturity profile (based on the system's previous data regarding similar plants). When the predicted trajectory of maturity meets a pre-defined goal (again, defined by the user or by the system/service) a predicted date and time of reaching that goal is produced. The produced date of reaching the goal (which may mean harvest time) can be sent to the user and provide them with value such as better logistic planning for the day of harvest, realization that maturity is too fast or too slow etc.

In an exemplary embodiment of the invention, growers may choose at what resolution to work in diagnosing each flower/flower cone at a time, each plant at a time or any other resolution.

In an exemplary embodiment of the invention, the system or method may supply growers with a dashboard-like software to visualize plants status in their facility, making large scale insight possible. In this software a visual interface may portray the diagnostic data accumulated by the system per each plant (or under other resolutions as discussed above), spatially and temporally, in layers of different data kinds. For example, the grower may view in one glance the location-caused variability in plant maturity, and to see if there is or isn't a correlation between maturity, mold detections, and other accumulated data (including environmental data from sensors and other sources).

In an exemplary embodiment of the invention, upon diagnosis the user may get offered paths of action (the above discussed suggestions) in light of that diagnosis, either as a DSS or as part of a fully automated system as described above. For example, when mold is detected, the system can offer the user several solutions such as: cut away the infected flower/check if your humidity is high/buy a specific fungicide. In that way the system not only diagnoses but offers helpful information, may offer discounts for using a specific brand, collects data on users' chosen course of action when faced with different diagnoses.

It is expected that during the life of a patent maturing from this application many relevant algorithms will be developed and the scope of some of the term is intended to include all such new technologies a priori. As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Features of the present invention, including method steps, which are described in the context of separate embodiments, may also be provided in combination in a single embodiment. Conversely, features of the invention, which is described for brevity in the context of a single embodiment or in a certain order may be provided separately, or in any suitable sub combination or in a different order. Any or all of computerized sensors, output devices or displays, processors, data storage and networks may be used as appropriate to implement any of the methods and apparatus shown and described herein.

What is claimed is:

1. A method for computerized assessment of the status of a Cannabaceae plant, using a neural network, said method comprising:
   (a) training a neural network to predict a THC value of a Cannabaceae plant, by providing said neural network with a plurality of (i) first set of photographic images of non-Cannabaceae plants; and (ii) second set of known photographic images of Cannabaceae plants, and an input THC value associated with each image from said second set of photographic images;
       wherein said input THC value is determined using results of chemical composition laboratory tests obtained with HPLC or GC or HPLC-MS or GC-MS test equipment and test methods, said tests performed on the Cannabaceae plants captured in said known photographic images;
   (b) providing a user with access to said trained neural network;
   (c) allowing said user to input an unknown photographic image of a Cannabaceae plant;
   (d) analyzing said unknown photographic image Cannabaceae plant using said trained neural network to obtain a predicted THC value;
   (e) extracting features from said unknown photographic image of a Cannabaceae plant using image processing, the features including shape, size, density and color of the trichomes imaged in the unknown photographic image;
   (f) calculating and outputting to said user, an output based on the predicted THC value or the features or a combination thereof, the output comprises at least one of: maturity of the plant for harvesting; assessment of post-production Cannabaceae plant product quality and price.

2. The method of claim 1, wherein in said step (c) a plurality of images originating from one plant are inputted, and the features extracted in step (e) further comprise the growth rate by at least one of: plant shape, and movement over time.

3. The method of claim 1, wherein the method further comprises detection of a phenotype of the Cannabaceae plant.

4. The method of claim 1, wherein said photography images are captured using a wavelength that is not in the visible spectrum or is wider than the visible spectrum.

5. The method of claim 1, wherein the said trained neural network comprises a plurality of neural networks connected in serial, or wherein said THC level is calculated using a post processing stage after running said plurality of neural networks in parallel.

6. The method of claim 1, wherein step (c) further comprises receiving non-macro photography images and auxiliary data related to said Cannabaceae plant and related to the environment where said photography image was captured.

7. The method of claim 1, wherein step (c) is further comprised of receiving a video capture or a 3D image capture of the Cannabaceae plant.

8. The method of claim 1, wherein step (c) is further comprised of receiving at least one of or a combination of (1) 3D image analysis, and (2) 3D modeling.

9. The method of claim 1, wherein step (c) is further comprised of receiving at least one of or a combination of (1) the name, ID and type of the user uploading the data; (2) the name, ID and type of the identity of the previous link in the distribution chain; and (3) the commercial name of the product.

10. The method of claim 1, further comprising performing identification of the presence on said unknown photographic image of a Cannabaceae plant, of at least one of: diseases, insects, and pests.

11. The method of claim 10, wherein said disease is selected from at least one of: mold, powdery mildew.

12. The method of claim 10, wherein said pest is selected from at least one of: acari, aphid, and arthopods.

13. A computerized system for assessment of the status of a Cannabaceae plant, using a neural network, said system comprising:
- one or more photographic imagers;
- one or more user terminals receiving image data from said one or more photographic imagers; and
- a computing subsystem comprising one or more processors and communication links connecting said one or more user terminals to said one or more processors, wherein the one or more processors are configured to perform the following steps:
  - (a) training a neural network to predict a THC value of a Cannabaceae plant, by providing said neural network from the user terminals with a plurality of (i) first set of photographic images of non-Cannabaceae plants; and (ii) second set of known photographic images of Cannabaceae plants, and an input THC value associated with each image from said second set of photographic images;
  - wherein said input THC value is determined using results of chemical composition laboratory tests obtained with HPLC or GC or HPLC-MS or GC-MS test equipment and test methods, said tests performed on the Cannabaceae plants captured in said known photographic images;
  - (b) opening to said user terminal with an access to said trained neural network;
  - (c) inputting an unknown photographic image of a Cannabaceae plant by said user terminal;
  - (d) performing an analysis of said unknown photographic image Cannabaceae plant using said trained neural network to obtain a predicted THC value;
  - (e) extracting features from said unknown photographic image of a Cannabaceae plant using image processing, the features including shape, size, density and color of the trichomes imaged in the unknown photographic image;
  - (f) calculating and reporting to said user terminal, an output based on the predicted THC value or the features or a combination thereof, the output comprises at least one of: maturity of the plant for harvesting; assessment of post-production Cannabaceae plant product quality and price.

14. The system of claim 13, wherein the user terminal is a mobile phone, a smartphone or a tablet.

15. The system of claim 13, wherein the communication links comprises at least one of or a combination of a personal area network, a local area network, a wide area network and the Internet.

16. The system of claim 13, wherein the processing subsystem is located inside or adjacent to the user terminal.

17. The system of claim 13, wherein the processing subsystem is in a remote server farm or in the cloud.

18. The system of claim 13, wherein the system includes functionality for automated purchase testing.

19. The system of claim 13, wherein the photographic imager comprises a camera subsystem of a smartphone and an optical magnification device that is adapted to be clipped-on to the said smartphone, and wherein the user terminal is implemented by the said smartphone.

20. The system of claim 13, wherein said image data is transferred from the photographic imager to the user terminal by WiFi, Bluetooth, or any other wireless communication link or USB, Ethernet or any other wire communication link.

21. A non-transitory computer readable storage medium containing instructions associated with characterization of a status of a Cannabaceae plant, using a neural network; the instructions when executed causing the following:
- (a) training a neural network to predict a THC level of a Cannabaceae plant, by providing said neural network from a user terminal, with a plurality of (i) first set of photographic images of non-Cannabaceae plants; and (ii) second set of known photographic images of Cannabaceae plants, and an input THC value associated with each image from said second set of photographic images;
  - wherein said input THC value is determined using results of chemical composition laboratory tests obtained with HPLC or GC or HPLC-MS or GC-MS test equipment and test methods, said tests performed on the Cannabaceae plants captured in said known photographic images;
- (b) opening to said user terminal with an access to said trained neural network;
- (c) inputting an unknown photographic image of a Cannabaceae plant by said user terminal;
- (d) performing an analysis of said unknown photographic image Cannabaceae plant using said trained neural network to obtain a THC value;
- (e) extracting features from said unknown photographic image of a Cannabaceae plant using image processing, the features including shape, size, density and color of the trichomes imaged in the unknown photographic image;
- (f) calculating and reporting to said user terminal, an output based on the THC level or the features or a combination thereof, the output comprises at least one of: maturity of the plant for harvesting; assessment of post-production Cannabaceae plant product quality and price.

* * * * *